United States Patent [19]
Goulet et al.

[11] Patent Number: 6,150,352
[45] Date of Patent: Nov. 21, 2000

[54] ANTAGONISTS OF GONADOTROPIN RELEASING HORMONE

[75] Inventors: Mark Goulet, Westfield; Eric E Allen, Somerset; Matthew J. Wyvratt, Jr., Mountainside; Jinlong Jiang, Wodbridge; Richard B. Toupence, Scotch Plains; Thomas F Walsh, Watchung; Feroze Ujjainwalla, Edison; Jonathan R Young, Dayton; Robert J. Devita, Westfield, all of N.J.

[73] Assignee: Merck & Co., Inc., Rahway, N.J.

[21] Appl. No.: 09/180,662

[22] PCT Filed: May 16, 1997

[86] PCT No.: PCT/US97/08432

§ 371 Date: Nov. 12, 1998

§ 102(e) Date: Nov. 12, 1998

[87] PCT Pub. No.: WO97/44339

PCT Pub. Date: Nov. 27, 1997

Related U.S. Application Data

[60] Provisional application No. 60/017,959, May 20, 1996.

[30] Foreign Application Priority Data

Jun. 19, 1996 [GB] United Kingdom .................. 9612796

[51] Int. Cl.[7] ........................ C07D 401/14; C07D 31/47; C07D 417/14; C07D 409/14; C07D 495/04; A61K 31/47

[52] U.S. Cl. .................... 514/210.21; 546/157; 546/155; 546/135; 546/146; 544/331; 544/328; 544/277; 544/363; 544/238; 544/405; 544/322; 544/333; 544/278; 544/319; 544/128; 544/235; 544/284; 544/353; 544/317; 514/312; 514/275; 514/256; 514/253; 514/258; 514/269; 514/266; 514/274; 514/210; 514/305; 514/307; 514/235.2; 514/248; 514/259

[58] Field of Search ...................... 546/157, 155, 546/135, 146; 544/331, 328, 277, 363, 405, 322, 333, 278, 238, 319, 128, 235, 284, 353, 317; 514/312, 275, 256, 253, 258, 269, 266, 274, 210, 305, 307, 235.2, 248, 259, 249

[56] References Cited

U.S. PATENT DOCUMENTS

| | | |
|---|---|---|
| 1,941,312 | 12/1933 | Miescher et al. .................... 260/42 |
| 3,025,299 | 3/1962 | Pfister et al. ........................ 260/289 |
| 5,175,151 | 12/1992 | Afonso et al. ....................... 514/63 |
| 5,252,584 | 10/1993 | Carling et al. ....................... 514/312 |
| 5,348,962 | 9/1994 | Kulagowski et al. ................ 514/312 |
| 5,412,104 | 5/1995 | Afonso et al. ....................... 548/525 |
| 5,614,532 | 3/1997 | Carling et al. ....................... 514/312 |

FOREIGN PATENT DOCUMENTS

| | | |
|---|---|---|
| 0 219 292 A2 | 4/1987 | European Pat. Off. . |
| 0 679 642 A1 | 4/1994 | European Pat. Off. . |
| 2 711 992 A1 | 3/1993 | France . |
| 44-16373 | 7/1969 | Japan . |
| 6 2395561 A2 | 12/1988 | Japan . |
| WO 93/10783 | 6/1993 | WIPO . |
| WO 93/11115 | 6/1993 | WIPO . |
| WO 95/28405 | 10/1995 | WIPO . |
| WO 95/29900 | 11/1995 | WIPO . |
| WO 97/14682 | 4/1997 | WIPO . |

OTHER PUBLICATIONS

Carling et al. 4–Substituted–3–phenylquinolin–2(1H)–ones, J. Med. Chem. 40: 754–765, Feb. 1997.

Ross, Chapter 2 in Goodman and Gilman's The Pharmacological Basis of Therapeutics, 8th Ed., Pergamon Press, pp. 33–35, 1990.

CAS Prointout for Nishimura et al., Japanese Journal Yakugaku Zasshi, 90(7) 818–828, 1970.

CAS Printout for US 5,614,532, 1997.

J. Med. Chem. vol. 32, pp. 2036–2038 (1989), by Clark, et al.

J. Heterocyclic Chem, vol. 26, pp. 281–284 (1989), by Yamaguchi, et al.

Monatshefte Fur Chemie, vol. 113, pp. 751–760 (1982), by Stadlbauer, et al.

Vestn. Slov. Kem. Drus., vol. 33, No. 3, pp. 271–281 (1986), by Stadlbauer, et al.

*Primary Examiner*—Mukund J. Shah
*Assistant Examiner*—Hong Liu
*Attorney, Agent, or Firm*—Elliott Korsen; Mark R. Daniel

[57] ABSTRACT

There are disclosed compounds of formula (I)

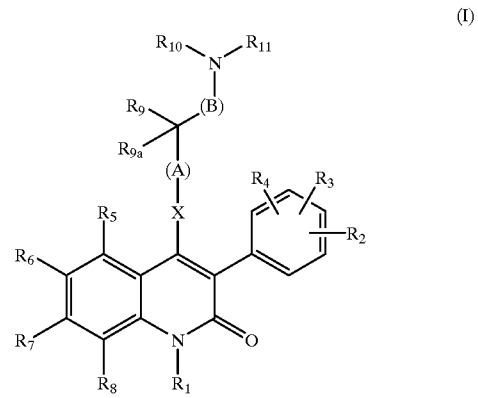

and pharmaceutically acceptable salts thereof which are useful as antagonists of GnRH and as such may be useful for the treatment of a variety of sex-hormone related conditions in both men and women.

10 Claims, No Drawings

ANTAGONISTS OF GONADOTROPIN RELEASING HORMONE

This application is a 371 of PCT/US97/08432, filed May 16, 1997 which claims benefit of Provisional Appl. 60/017,959 filed May 20, 1996.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or episteride; a 5α-reductase 1 inhibitor such as 4,7β-dimethyl-4-aza-5α-cholestan-3-one, 3-oxo-4-aza-4, 7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-i blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral adminstration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Arylquinolone analogs have been described in the art and include those described in the following patents, patent applications and journal articles. JP-A-63-295561 discloses a class of 3-phenyl-2(1H)-quinolone derivatives, substituted at the 4-position by an unsubstituted straight or branched alkoxy group and at the 7-position by an unsubstituted straight or branched alkoxy group. These compounds are alleged to exhibit a strong inhibitory action on bone resorption and a stimulatory effect on ossification, and thus to be useful as therapeutic agents for the prevention and treatment of osteoporosis.

J. Heterocycl. Chem., 1989, 26, 281 discloses a range of 3-(2-methoxyphenyl)-2(1H)-quinolones possessing a halogen substituent in the 6- or 7-position and an optional carboxylic acid substituent at the 4-position. A family of 3-phenyl-2(IH)-quinolone derivatives, substituted at the 4-position by an amino or benzylamino group and at the 7-position by a methyl or methoxy group, is described in Monatsh. Chem., 1982, 113, 751 and Vestn. Slov. Kem. Drus., 1986, 33, 271.

WO 93/10783 and WO 93/11115 disclose a class of 2-(1H)-quinolone derivatives, substituted at the 3-position by an optionally substituted aryl substituent and are selective non-competitive antagonists of NMDA receptors and/or are antagonists of AMPA receptors, and are therefore of utility in the treatment of conditions, such as neurodegenerative disorders, convulsions or schizophrenia.

FR 2711992-Al discloses quinolone derivatives which are allegedly useful as antagonists of platelet activating factor.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase I and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

DETAILED DESCRIPTION OF THE INVENTION

The present invention relates to compounds of the general formula (I)

wherein:

A is a bond, $C_1-C_6$ alkyl, substituted $C_1-C_6$ alkyl, $C_2-C_6$ alkenyl, substituted $C_2-C_6$ alkenyl, $C_2-C_6$ alkynyl, substituted $C_2-C_6$ alkynyl, $C_1-C_6$ alkoxy, substituted $C_1-C_6$ alkoxy;

B is a bond, $C_1-C_4$ alkyl, substituted $C_1-C_4$ alkyl;

X is O, S, SO, $SO_2$, $NR_{12}$, $C(R_{13}R_{14})$ or can be absent;

$R_1$ is H, $C_1-C_6$ alkyl, substituted $C_1-C_6$ alkyl, $C_3-C_6$ cycloalkyl, substituted $C_3-C_6$ cycloalkyl, aryl, substituted aryl, $C_1-C_6$ aralkyl, substituted $C_1-C_6$ aralkyl;

$R_2$, $R_3$ and $R_4$ are independently H, $C_1-C_6$ alkyl, substituted $C_1-C_6$ alkyl, $C_2-C_6$ alkenyl, substituted $C_2-C_6$ alkenyl, $C_2-C_6$ alkynyl, substituted $C_2-C_6$ alkynyl, CN, nitro, $C_1-C_3$ perfluoroalkyl, $C_1-C_3$ perfluoroalkoxy, aryl, substituted aryl, $C_1-C_6$ aralkyl, substituted $C_1-C_6$ aralkyl, $R_{15}O(CR_{13}R_{14})_p—$, $R_{16}C(O)O(CR_{13}R_{14})_p—$, $R_{15}OC(O)(CR_{13}R_{14})_p—$, $—(CR_{13}R_{14})_pS(O)_nR_{12}$, $(CR_{13}R_{14})_pC(O)NR_{17}R_{18}$, $—(CR_{13}R_{14})_pNR_{17}C(O)R_{16}$, $—(CR_{13}R_{14})_pN(R_{17}R_{18})$ or halogen;

$R_2$ and $R_3$ taken together form a carbocyclic ring, saturated or unsaturated, of 3–7 carbon atoms or a heterocyclic ring containing 1–3 heteroatoms selected from N, O and S;

$R_5$, $R_6$, $R_7$ and $R_8$, independently are H, halogen, $C_1-C_6$ alkyl, substituted $C_1-C_6$ alkyl, $C_2-C_6$ alkenyl, substituted $C_2-C_6$ alkenyl, $C_2-C_6$ alkynyl, substituted $C_2-C_6$ alkynyl, aryl, substituted aryl, $C_1-C_6$ aralkyl, substituted $C_1-C_6$ aralkyl, heteroaryl, $C_1-C_6$ heteroaralkyl, substituted heteroaryl, substituted $C_1-C_6$ heteroaralkyl, $C_1-C_3$ perfluoroalkyl, $C_1-C_3$ perfluoroalkoxy, $R_{15}O(CR_{13}R_{14})_p—$, $—(CR_{13}R_{14})_pCN$, $—(CR_{13}R_{14})_pSO_nR_{12}$, $—(CR_{13}R_{14})_pSO_2N(R_{17}R_{18})$, $—(CR_{13}R_{14})_pN(R_{17}R_{18})$, $—(CR_{13}R_{14})_pN(R_{17})C(O)R_{16}$, $—(CR_{13}R_{14})_pN(R_{17})C(O)N(R_{17}R_{18})$, $—(CR_{13}R_{14})_pN(R_{17})SO_2N(R_{17}R_{18})$, $—(CR_{13}R_{14})_pN(R_{17})SO_2R_{12}$, $—(CR_{13}R_{14})_pC(O)OR_{15}$, $—(CR_{13}R_{14})_pOC(O)R_{16}$, $—(CR_{13}R_{14})_pC(O)N(R_{17}R_{18})$ $—(CR_{13}R_{14})_pOC(O)N(R_{17}R_{18})$, $—(CR_{13}R_{14})_pN(R_{17})C(O)OR_{15}$, or $$—(CR_{13}R_{14})_pN(R_{17})\underset{\underset{N—R_{19}}{\|}}{C}(NR_{17}R_{18})$$

$R_9$ and $R_{9a}$ are independently H, $C_1-C_6$ alkyl, substituted $C_1-C_6$ alkyl, aryl, $C_1-C_6$ aralkyl, substituted aryl, substituted $C_1-C_6$ aralkyl; or $R_{10}$ is H, $C_1-C_6$ alkyl, substituted $C_1-C_6$ alkyl, aryl, $C_1-C_6$ aralkyl, substituted aryl, substituted $C_1-C_6$ aralkyl; or $R_{11}$ is H, $C_1-C_6$ alkyl, substituted $C_1-C_6$ alkyl, $—(CR_{13}R_{14})_pC(O)OR_{15}$; or $R_9$ and $R_{9a}$ can be taken together to form a carbocyclic ring, saturated or unsaturated, of 3–7 variously substituted carbon atoms, or;

$R_9$ and $R_{10}$ can be taken together to form a heterocyclic ring, saturated or unsaturated, of 4–7 atoms containing 1–3 heteroatoms selected from O, N, and S, or;

($R_9$ and $R_{10}$) and ($R_{9a}$ and $R_{11}$) can be taken together to form a heterobicyclic ring, with each ring being independently saturated or unsaturated, of 4–7 atoms containing 1–3 heteroatoms selected from O, N, and S;

$R_{12}$ is H, $C_1-C_6$ alkyl, substituted $C_1-C_6$ alkyl, aryl, substituted aryl, $C_1-C_6$ aralkyl, substituted $C_1-C_6$ aralkyl;

$R_{13}$ and $R_{14}$ are independently H, $C_1-C_6$ alkyl, substituted $C_1-C_6$ alkyl, aryl, substituted aryl, $C_1-C_6$ aralkyl, substituted $C_1-C_6$ aralkyl;

$R_{15}$ is H, $C_1-C_6$ alkyl, substituted $C_1-C_6$ alkyl, aryl, substituted aryl, $C_1-C_6$ aralkyl, substituted $C_1-C_6$ aralkyl; heteroaryl, substituted heteroaryl, $C_1-C_6$ heteroaralkyl, substituted $C_1-C_6$ heteroaralkyl, or a heterocyclic ring containing 1–4 heteroatoms selected from O, N, and S;

$R_{16}$ is H, $C_1-C_6$ alkyl, substituted $C_1-C_6$ alkyl, aryl, substituted aryl, $C_1-C_6$ aralkyl, substituted $C_1-C_6$ aralkyl; heteroaryl, substituted heteroaryl, $C_1-C_6$ heteroaralkyl, substituted $C_1-C_6$ heteroaralkyl, or a heterocyclic ring containing 1–4 heteroatoms selected from O, N, and S;

$R_{17}$ and $R_{18}$ are independently H, $C_1-C_6$ alkyl, substituted $C_1-C_6$ alkyl, $C_3-C_6$ cycloalkyl, substituted $C_3-C_6$ cycloalkyl, aryl, substituted aryl, $C_1-C_6$ aralkyl, substituted $C_1-C_6$ aralkyl, heteroaryl, substituted heteroaryl, $C_1-C_6$ heteroaralkyl, substituted $C_1-C_6$ heteroaralkyl; or taken together form a carbocyclic ring(s) of 4–7 carbon atoms each or a heterocyclic ring containing 1–4 heteroatoms selected from O, N, and S;

$R_{19}$ is H, $C_1$–$C_6$ alkyl, substituted $C_1$–$C_6$ alkyl or —CN;

n is 0, 1, or 2;

p is 0, 1, 2, 3 or 4 the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "halogen" or "halo" is intended to include fluorine, chlorine, bromine and iodine.

The term "aryl" includes phenyl and naphthyl. Preferably, aryl is phenyl.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

The term "heteroaryl" is intended to include the compounds shown below:

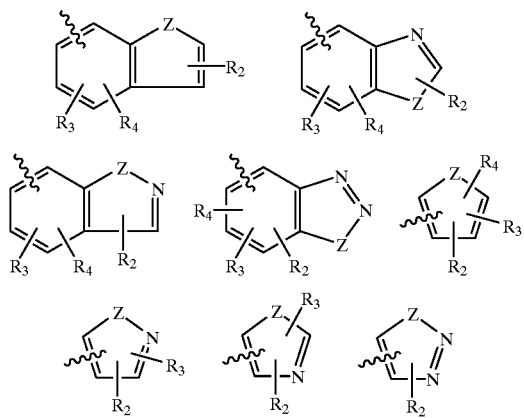

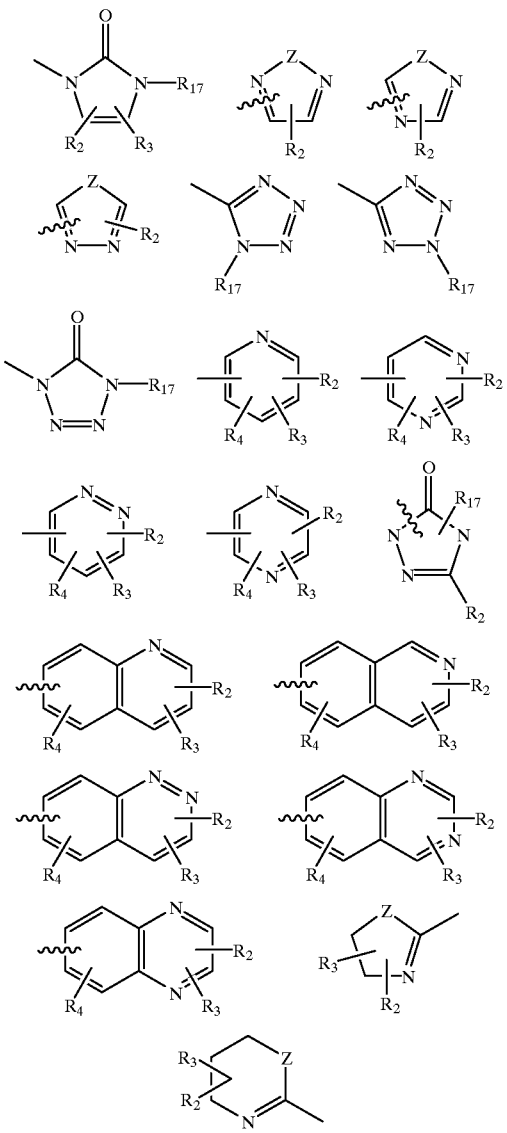

where Z is: O, S, or $NR_{12}$

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical fomula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methanesulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

As used herein, the term "composition" is intended to encompass a product comprising the specified ingredients in the specified amounts, as well as any product which results, directly or indirectly, from combination of the specified ingredients in the specified amounts.

The compounds of the invention are prepared by the following reaction schemes. All substituents are as defined above unless indicated otherwise.

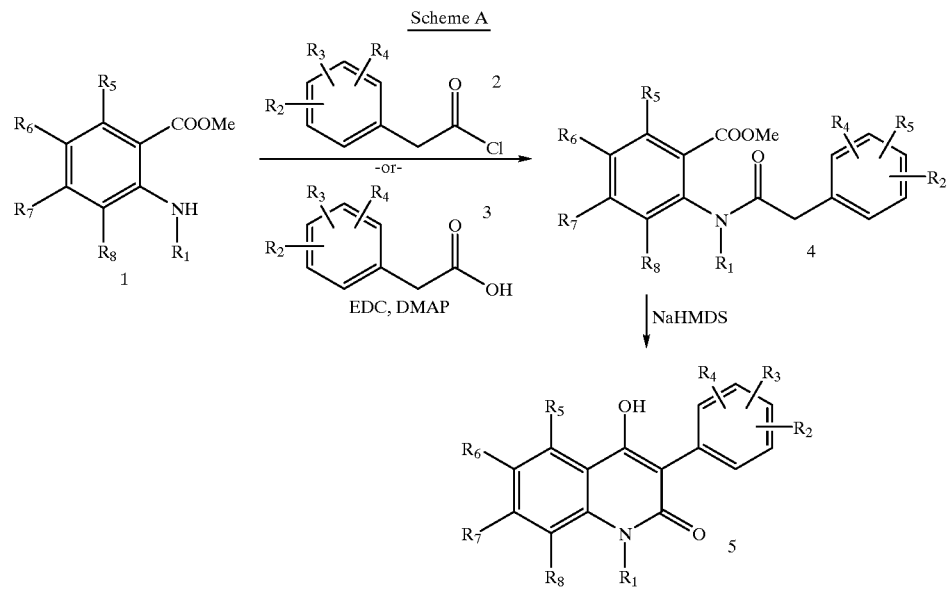

Reaction Scheme A

As shown in reaction Scheme A, treatment of amino ester (1) with an aryl acetyl chloride (2) in an inert organic solvent such as dicloroethane, chloroform, methylene chloride or the like at a temperature of 25°–80° C. for a period of 30 minutes to 4 hours gives the corresponding amide (4). Alternatively, treatment of amine (1) and an arylacetic acid (3) with the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide derivative (4). Cyclization of amide (4) is effected by treatment with a strong base such as sodium bis(trimethylsilyl)amide, lithium bis(trimethylsilyl)amide or the like in an inert organic solvent such as tetrahydrofuran at a temperature of −20°–25° C. for a period of 2–4 hours to give quinolone (5).

Scheme B

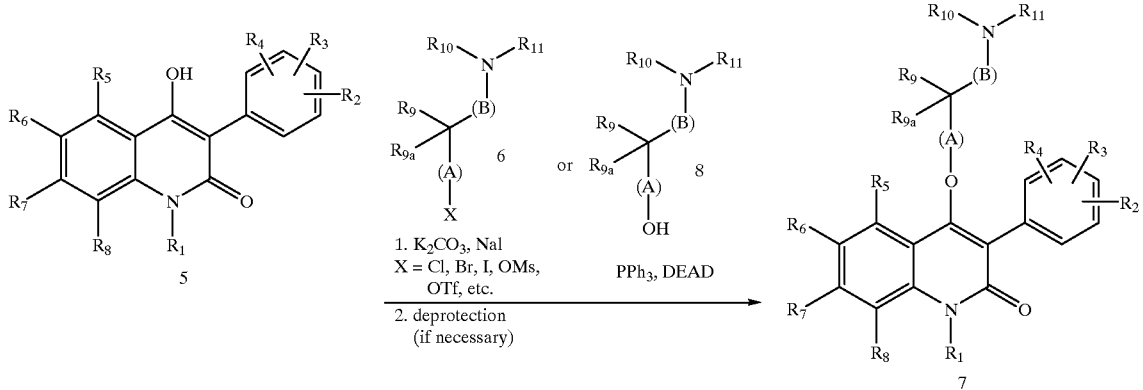

Reaction Scheme B

As shown in reaction Scheme B, treatment of the 4-hydroxyquinolone (5) with an alkylamine containing a halogen or sulfonate leaving group (6) and a suitable base such as potassium carbonate, sodium carbonate, sodium bicarbonate, DBU or the like along with the catalyst sodium iodide in an inert organic solvent such as N,N-dimethylformamide, tetrahydrofuran, acetonitrile or the like at or around 80° C. for a period of 4–24 hours provides the ether derivative (7). As an alternative, a suitably protected amino alcohol (8) may be coupled to (5) by treatment under Mitsunobu reaction conditions with triphenylphosphine and an activating agent such as diethyl azodicarboxylate, diisopropyl azodicarboxylate or the like in an inert solvent such as tetrahydrofuran, toluene, chlorobenzene or the like at ambient temperature for a period of 4–64 hours to give (7).

After coupling, the amino group can be deprotected by any method suitable to the protecting group used and compatible with the functionality present in (7). For example, a t-butyl carbamate group can be removed by treatment with a protic acid such as trifluoroacetic acid, with or without added anisole, in an inert organic solvent such as methylene chloride at ambient temperature for a period of 30 minutes to 4 hours to provide the corresponding amine.

Scheme C

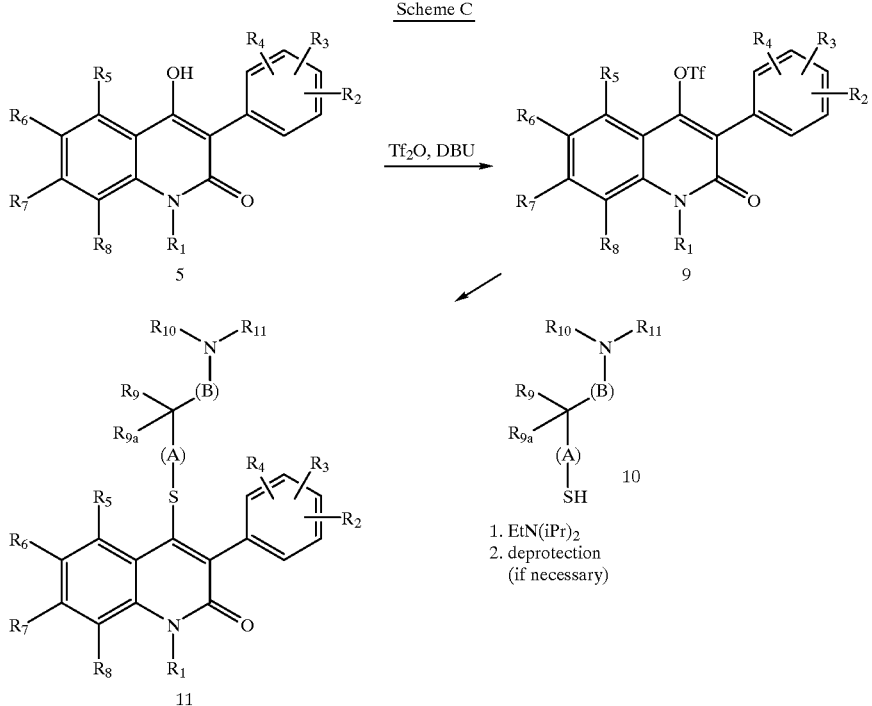

Reaction Scheme C

As shown in reaction Scheme C, the 4-hydroxyquinolone structure (5) may be modified by conversion to a sulfonate leaving group such as the trifluoromethanesulfonate (9) upon treatment with trifluoromethane-sulfonic anhydride in an inert organic solvent such as methylene chloride and an amine base such as diazabicycloundecene, 2,6-lutidine, pyridine or the like at or below room temperature for a period of 30 minutes to 2 hours. Reaction of (9) with an appropriate thiol (10) and an amine base such as diisopropylethylamine, triethylamine or the like in an inert organic solvent such as N,N-dimethylformamide at or below room temperature for a period of 4–24 hours gives the thioether analog (11).

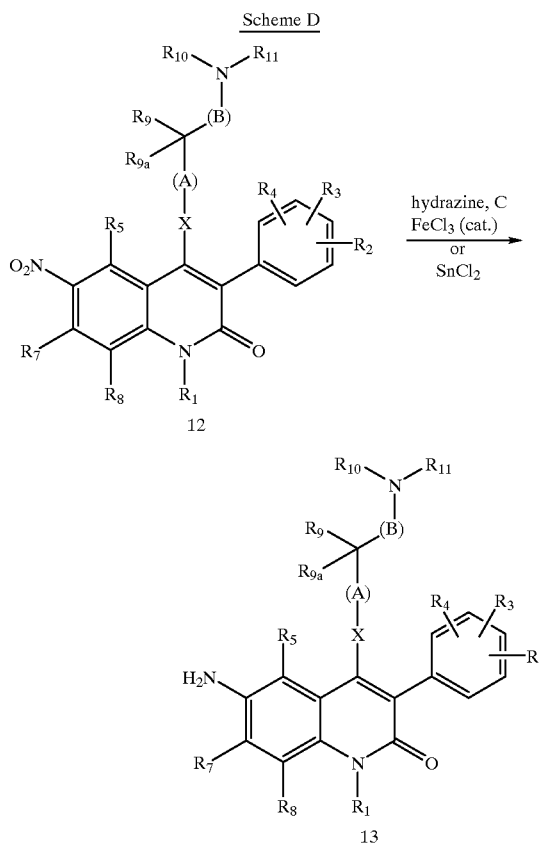

Reaction Scheme D

As shown in reaction Scheme D, nitro groups appended to these structures, such as in (12), can be reduced to the corresponding amines (13) by treatment with hydrazine and a reduction catalyst such as iron (III) chloride and carbon in an inert organic solvent such as methanol, ethanol or the like at a temperature of 65°–100° C. for a period of 5–20 hours. Alternatively, treatment of (12) with tin(II)chloride dihydrate in a polar solvent such as ethanol or methanol at a temperature of 70°–80° C. for a period of 30 minutes to 4 hours gives the reduced, amino derivative (13).

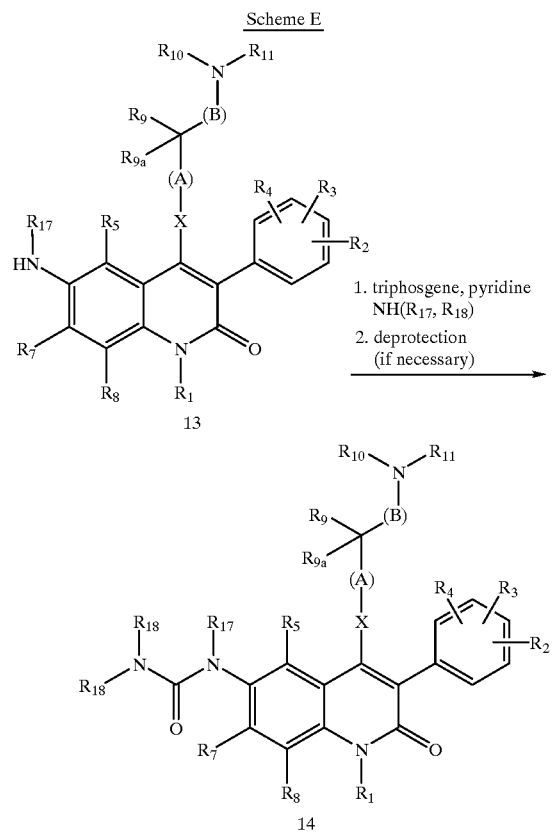

Reaction Scheme E

As shown in reaction Scheme E, amines such as (13) can be converted to the corresponding urea derivatives (14) by treatment with an appropriate acylating agent such as phosgene, triphosgene, carbonyldiimidazole or the like, with or without an amine base such as pyridine in an inert organic solvent such as methylene chloride, chloroform, dicloroethane or the like together with the desired primary or secondary amine at 0°–25° C. for a period of 1–48 hours.

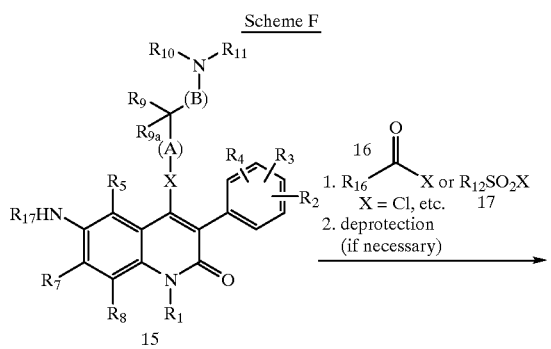

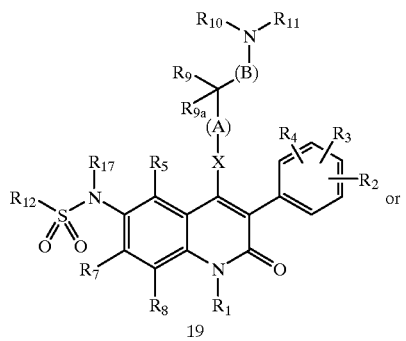

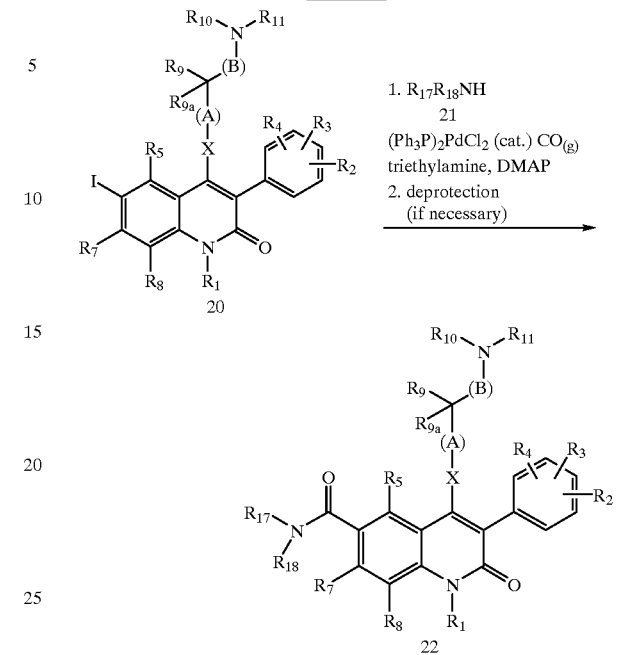

Scheme G

Reaction Scheme F

As shown in reaction Scheme F. amines such as (15) can be converted to the corresponding amide (18) or sulfonamide derivatives (19) by treatment with an appropriate acylating agent such as an acetyl chloride, acid anhydride, sulfonylchloride, sulfonic anhydride or the like, with or without an amine base such as pyridine, in an inert organic solvent such as methylene chloride, chloroform, dichloroethane, benzene, toluene, chlorobenzene or the like at 0°–100° C. for a period of 1–10 hours.

Reaction Scheme G

As shown in Scheme G, iodides such as (20) can be converted to the corresponding amide (22) by treatment with an appropriate amine (21) and a palladium catalyst such as dichlorobis(triphenylphosphine)palladium(II) in the presence of an amine base such as triethylamine in an inert organic solvent such as N,N-dimethylformamide, or the like, under an atmosphere of carbon monoxide at 90° C. for a period of 5–25 hours.

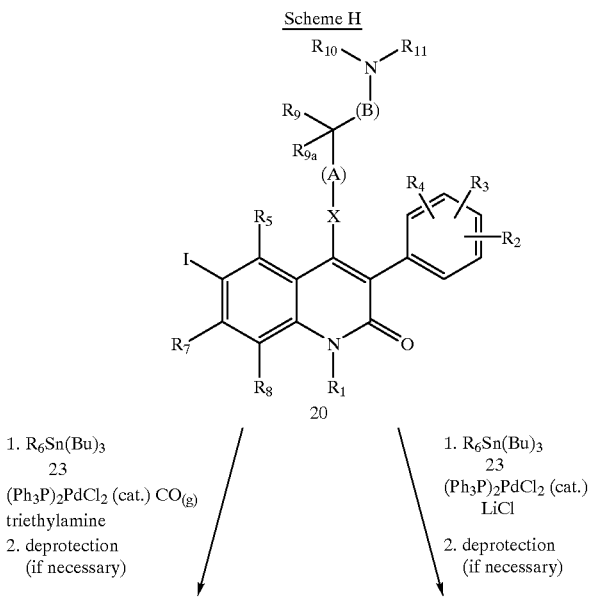

Scheme H

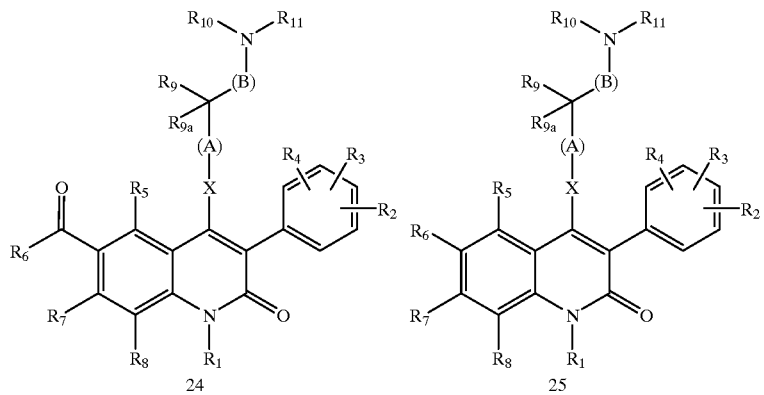

Reaction Scheme H

As shown in Reaction Scheme H, iodide (20) can be coupled with alkyl-, vinyl-, aryl- and heteroaryl-stannanes (23) using an appropriate palladium catalyst such as dichlorobis(triphenylphosphine) palladium(II) in an inert organic solvent such as N,N-dimethyl formamide, toluene, or the like, at a temperature of 80–110° C. with or without the presence of carbon monoxide to provide ketones (24) and carbon-linked derivatives (25), respectively.

Scheme I

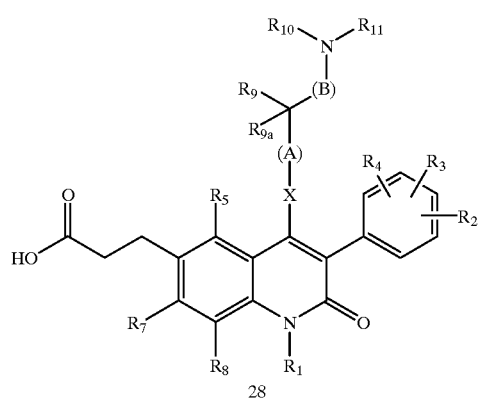

Reaction Scheme I

As shown in Scheme I, the allyl derivative (26) can be converted to primary alcohol (27) by treatment with borane or a suitable alkylborane reagent in an inert solvent such as tetrahydrofuran followed by exposure to a mild oxidant such as hydrogen peroxide. Alcohols such as (27) can be further oxidized by treatment with tetrapropylammonium perruthenate(VII) and 4-methylmorpholine-N-oxide or similarly mild oxidants in an organic solvent such as methylene chloride at room temperature for a period of 1 to 5 hours to give the corresponding aldehyde. Further oxidation to the carboxylic acid can be conducted with a strong oxidant such as potassium permanganate to give acids such as (28).

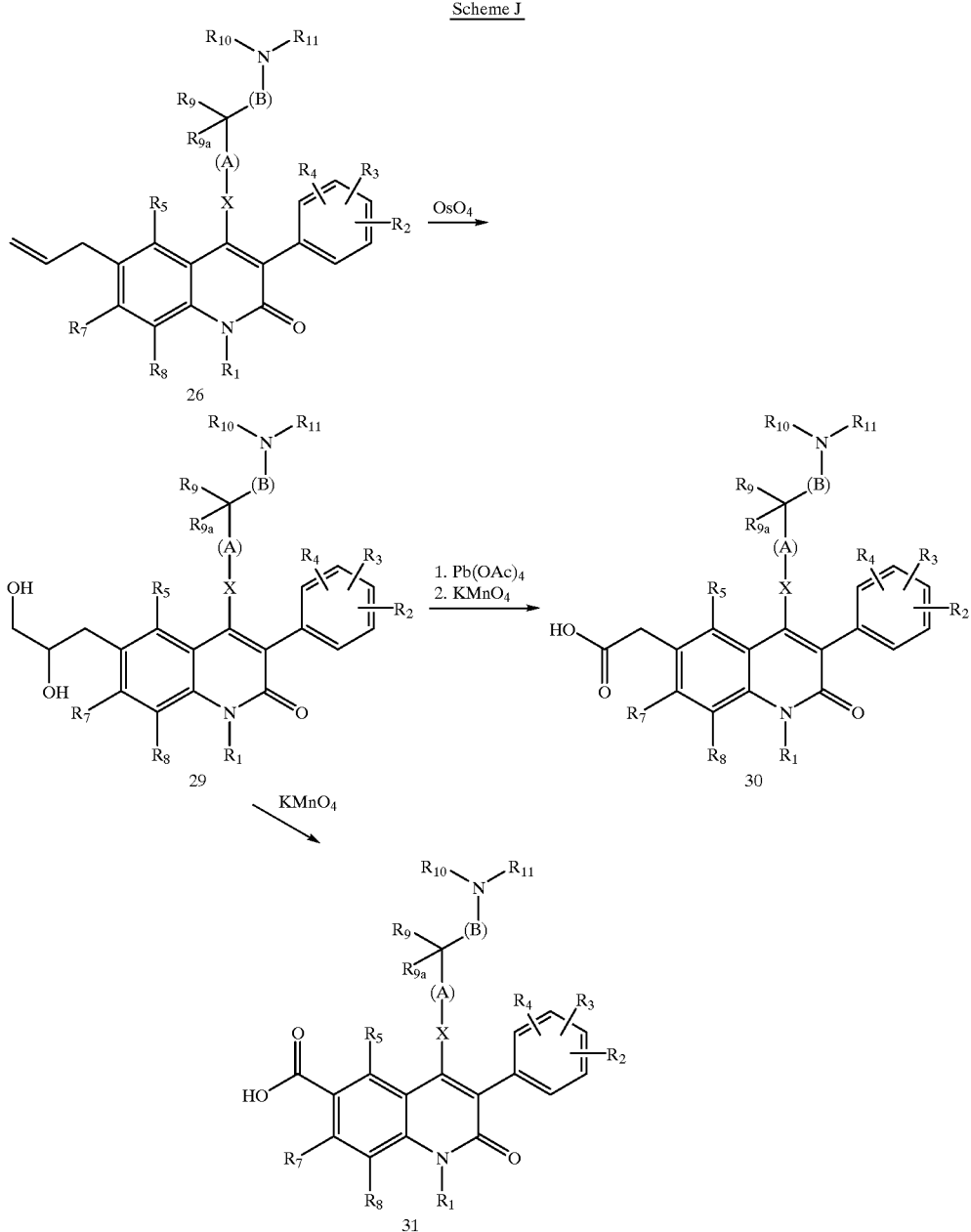

Reaction Scheme J

As shown in Scheme J, the allyl derivative (26) can be converted to the diol (29) by treatment with osmium tetraoxide with or without a co-oxidant such as 4-methylmorpholine-N-oxide in an inert solvent such as tetrahydrofuran, tert-butanol, water or mixtures thereof at room temperature for a period of 15 minutes to 5 hours. Diols such as (29) can be further oxidized by treatment with lead (IV) acetate in an inert solvent such as methanol pyridine or mixtures thereof at room temperature for a period of 10 minutes to 2 hours to give the corresponding aldehyde derivative. Further oxidation to the carboxylic acid can be conducted with a strong oxidant such as potassium permanganate to give acids such as (30).

Alternatively, treatment of diol (29) with a strong oxidant such as potassium permanganate, ruthenium tetraoxide or the like can give the benzoic acid product (31) directly.

Scheme K

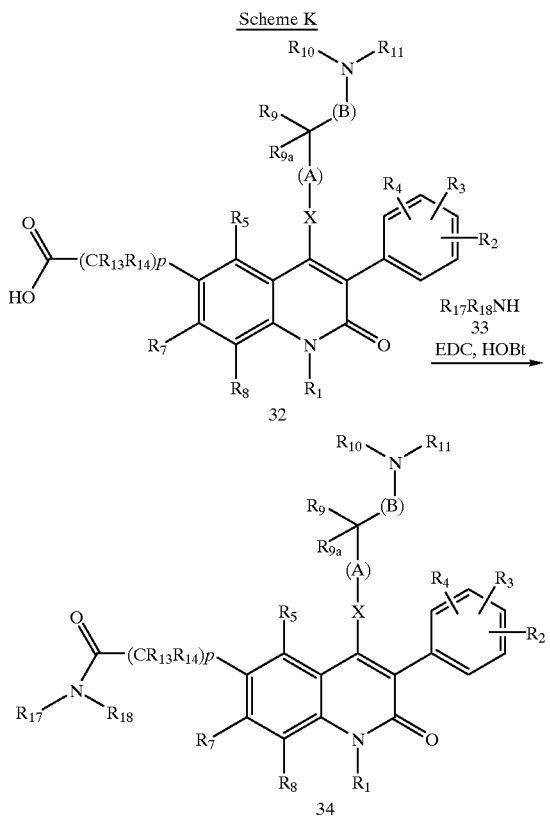

Reaction Scheme K

As shown in Scheme K, treatment of carboxylic acid (32) and an appropriate amine such as (33) with the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine NMM), triethylamine or the like in an inert organic solvent such as methylene chloride, chloroform, dimethylformamide, or mixtures thereof at or near room temperature for a period of 3–24 hours provides the corresponding amide derivative (34).

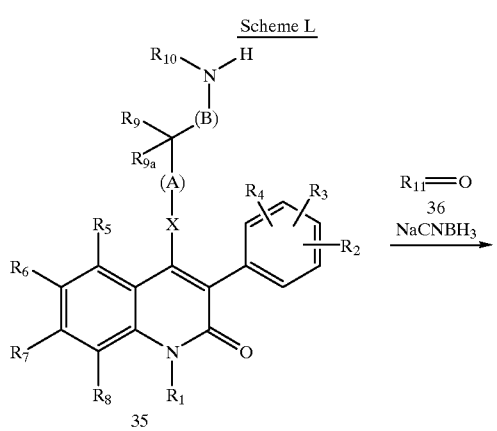

Scheme L

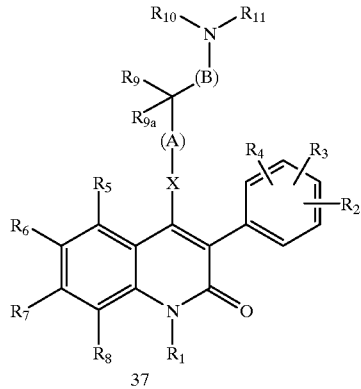

Reaction Scheme L

As shown in Scheme L, amines such as (35) can undergo reductive amination with carbonyl -containing compounds like (36) by treating the pair with a dessicant such as molecular seives or magnesium sulfate and an acid catalyst such as acetic acid in an inert organic solvent such as methanol, chloroform or the like followed by a reducing agent such as sodium cyanoborohydride, sodium borohydride, or hydrogen and an appropriate metal catalyst to give derivative (37).

The compounds of the present invention are useful in the treatment of various sex-hormone related conditions in men and women. This utility is manifested in their ability to act as antagonists of the neuropeptide hormone GnRH as demonstrated by activity in the following in vitro assays.

Human GnRH receptor binding assay

Crude membranes prepared from CHO cells expressing human GnRH receptors were the sources for GnRH receptor. [$^{125}$I]Buserelin (a peptidyl GnRH analog) was used as the radiolabelled ligand. The binding activity was determined as an $IC_{50}$ which is the antagonist concentration required to inhibit the specific binding of [$^{125}$I]buserelin to GnRH receptors by 50%.

Rat pituitary GnRH receptor binding assay

Crude plasma membranes prepared from rat pituitary tissues were incubated in a Tris.HCl buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH release assay

Active compounds from the GnRH receptor binding assay were further evaluated with an in vitro LH release assay to confirm their antagonist activity (blocking OnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-ml polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-ml disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of $3 \times 10^5$ cells/mL, and 1.0 mL of this suspension was placed in each well of a 24-well tray (Costar, Cambridge, Mass.). Cells were maintained in a humidified 5% $CO_2$-95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1 ½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. Nos. 3,239,345; 4,036,979; 4,411,890; 5,206,235; 5,283,241; 5,284,841; 5,310,737; 5,317,017; 5,374,721; 5,430,144; 5,434,261; 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94111012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methyl-propanamide;
2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methyl-propanamide;
3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methyl-propanamide;
4) N-[1(R)-[(3,4-Dihydro-spiro[2H-1-benzopyran-2,4'-piperidin]-1'-yl)carbonyl] -2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro[3H-indole-3,4'-piperidin]-1'-yl)carbonyl]-2-

(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methyl-propanamide;

12) N-[1(R)-[(1,2-Dihydro-1-methanesulfonylspiro[3H-indole-3,4'-piperidin]- 1'-yl)carbonyl]-3-cyclohexylpropyl]-2-amino-2-methyl-propanamide;

13) N-[1(R)-[(1,2-Dihydro-1-methanesulfonylspiro[3H-indole-3,4'-piperidin]-1'-yl)carbonyl]-4-phenylbutyl]-2-amino-2-methyl-propanamide;

14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;

15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;

16) N-[1(R)-[(1,2-Dihydro-1-(2-ethoxycarbonyl)methylsulfonylspiro-[3H-indole-3,4'-piperidin]-1'-yl)carbonyl]-2-(1H-indol-3-yl)ethyl]-2-amino-2-methylpropanamide;

17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. Nos. 3,251,907; 3,422,137; 3,584,125; 3,940,436; 3,944,599; 3,962,432; 4,054,598; 4,267,108; 4,327,039; 4,407,761; 4,578,376; 4,621,077; 4,624,947; 4,746,654; 4,761,406; 4,922,007; 4,942,157; 5,227,506; 5,270,365; EPO Patent Pub. No. 0,252,504; and J. Org. Chem., 36, 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 10 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

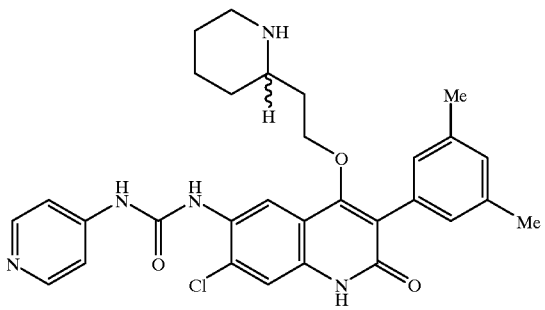

1-[7-chloro-3-(3,5-dimethylphenyl)-2-oxo-4-(2-piperidin-2-yl-ethoxy)-1,2-dihydro-quinolin-6-yl]-3-pyridin-4-yl-urea Step 1A 4-chloro-2-[2-(3,5-dimethylphenyl)-acetylamino]-5-nitro-benzoic acid methyl ester To a suspension of 2-amino-4-chloro-5-nitrobenzoic acid methyl ester (989 mg in 15 mL of dry 1,2-dichloroethane) was added a solution of (3,5-dimethylphenyl)acetyl chloride (860 mg in 5 mL dry 1,2-dichloroethane) and the mixture heated at reflux on an oil bath. After 18 hours, an additional portion of (3,5-dimethylphenyl)acetyl chloride (274 mg in 1.5 mL dry 1,2-dichloroethane) was added and the mixture heated at reflux for an additional 5 hours. At this time the reaction was cooled and the solvent removed in vacuo. Recrystallization of the crude product from methanol gave the title compound (1.17 g).

Step 1B 7-chloro-3-(3,5-dimethylphenyl)-4-hydroxy-6-nitro-1H-quinolin-2-one

To a solution of 4-chloro-2-[2-(3,5-dimethylphenyl)-acetylamino]-5-nitrobenzoic acid methyl ester (1.17 g in 10 mL dry tetrahydrofuran) at 0° C. was added dropwise a solution of sodium bis(trimethylsilyl)amide (7.8 mL of a 1.0M solution in tetrahydrofuran) and the mixture warmed to room temperature. After 2 hours, the reaction was quenched by the addition of 100 mL iced 6N hydrochloric acid. The slurry was stirred for 10 minutes then filtered and washed (2x) with ice water and then cold acetonitrile. The residue was dried overnight at 45° C. to give the title compound (970 mg).

Step 1C 2-{2-[6-nitro-7-chloro-3-(3,5-dimethylphenyl)-2-oxo-1,2-dihydroquinolin-4-yloxy]-ethyl}-piperidine-1-carboxylic acid benzyl ester To a solution of 7-chloro-3-(3,5-dimethylphenyl)-4-hydroxy-6-nitro-1H-quinolin-2-one (13.5 g in 600 mL of N,N-dimethylformamide) was added 9.2 g of 2-(2-hydroxyethyl)-piperidine-1-carboxylic acid benzyl ester and 14 g of triphenylphosphine followed by 10.4 mL of diisopropyl azodicarboxylate and the mixture stirred at room temperature. After 24 hours, the solvents were removed in vacuo and the residue resolvated in methylene chloride, washed with water and purified by flash chromatography on silica gel (hexane:ethyl acetate, 90:10; then methylene chloride:ethyl acetate, 95:5) to give the title compound (13.2 g).

Step 1D 2-{2-[6-amino-7-chloro-3-(3,5-dimethylphenyl)-2-oxo-1,2-dihydroquinolin-4-yloxy]-ethyl}-piperidine-1-carboxylic acid benzyl ester To a solution of 2-{2-[6-nitro-7-chloro-3-(3,5-dimethylphenyl)-2-oxo-1,2-dihydroquinolin-4-yloxy]-ethyl}-piperidine-1-carboxylic acid benzyl ester (1.11 g in 30 mL ethanol) was added 2 mL tin(II)chloride dihydrate and the mixture heated to 70° C. on an oil bath. After 2 hours, the reaction was cooled to room temperature and quenched by the addition of 300 mL ice-water. The acidity of the resulting solution was adjusted to pH 8 by the addition of saturated aqueous sodium bicarbonate and the mixture extracted (2x) with ethyl acetate. The combined organics were washed with brine, dried over sodium sulfate and concentrated in vacuo. Purification of the crude oil by flash chromatography on silica gel (methylene chloride:ethyl acetate, 95:5) gave the title compound (0.50 g).

Step 1E 2-{2-[7-chloro-3-(3,5-dimethylphenyl)-2-oxo-6-(3-pyridin-4-yl-ureido)-1,2-dihydroquinolin-4-yloxy]-ethyl}-piperidine-1-carboxylic acid benzyl ester To a solution of 2-{2-[6-amino-7-chloro-3-(3,5-dimethylphenyl)-2-oxo-1,2-dihydroquinolin-4-yloxy]-ethyl}-piperidine-1-carboxylic acid benzyl ester (200 mg in 5 mL dry methylene chloride) at 0° C. was added phosgene (0.3 mL of a 1.93 M solution in toluene) followed by 0.111 mL of triethylamine and the mixture stirred for 1 hour at 0° C. At this time, 188 mg of 4-aminopyridine was added and the mixture allowed to warm to room temperature. After 20 hours, the mixture was diluted with ethyl acetate (200 mL) and the reaction quenched by the addition of 10% citric acid. The organic portion was concentrated in vacuo to provide the crude title compound.

Step 1F 1-[7-chloro-3-(3,5-dimethylphenyl)-2-oxo-4-(2-piperidin-2-yl-ethoxy)-1,2-dihydro-quinolin-6-yl]-3-pyridin-4-yl-urea A solution of 2-{2-[7-chloro-3-(3,5-dimethylphenyl)-2-oxo-6-(3-pyridin-4-yl-ureido)-1,2-dihydroquinolin-4-yloxy]-ethyl}-piperidine-1-carboxylic acid benzyl ester in 3 mL of a 30% solution of hydrobromic acid in acetic acid was stirred at room temperature for 3 hours then concentrated in vacuo. The residue was treated with saturated sodium bicarbonate and then extracted with ethyl acetate. Purification of the concentrate by flash chromatography on silica gel (methylene chloride:methanol:ammonium hydroxide, 96:3:1) gave the title compound.

PREPARATION OF SYNTHETIC INTERMEDIATES 2-amino-4-chloro-5-nitrobenzoic acid methyl ester Step A: 2-acetylamino-4-chloro-5-nitrobenzoic acid methyl ester To a solution of 3 mL conc. sulfuric acid and 0.40 mL of 90% nitric acid at 0° C. was added 2-acetylamino-4-chlorobenzoic acid methyl ester (1.5 g) in three portions over a period of 20 minutes. This was stirred at 0° C. for 30 minutes then allowed to warm to room temperature for an additional 1 hour. At this time the reaction was poured into 50 mL of an ice/water mixture and extracted with ethyl acetate (3x50 mL). The combined organics were washed sequentially with water (2x50 mL), 10% sodium bicarbonate (2x50 mL) and brine (50 mL) then dried over magnesium sulfate and concentrated in vacuo. Recrystallization of the crude product from methanol gave the title compound (1.02 g).

Step B: 2-amino-4-chloro-5-nitrobenzoic acid methyl ester

To a solution of 2-acetylamino-4-chloro-5-nitrobenzoic acid methyl ester (1.02 g in 15 mL methanol) was added 1 mL of conc. sulfuric acid and the mixture heated to reflux on an oil bath. After 1 hour, the mixture was concentrated in vacuo and the resulting solid dissolved in 200 mL ethyl acetate. This was then washed with 10% sodium bicarbonate (2×100 mL) and brine (100 mL) and the organics dried over magnesium sulfate. The concentrate was recrystallized from methanol to give the title compound (0.82 g).

(3,5-dimethylphenyl)acetyl chloride

To a solution of (3,5-dimethylphenyl)acetic acid (2.32 g in 25 mL dry methylene chloride) at 0° C. was added 0.055 mL N,N-dimethylformamide followed by the dropwise addition of 1.3 mL of oxalyl chloride. After 15 minutes the mixture was warmed to room temperature and stirred for an additional 2 hours. Removal of the solvents in vacuo provided the title compound which was used without purification.

Following a procedure similar to that described above, the following compounds were prepared:

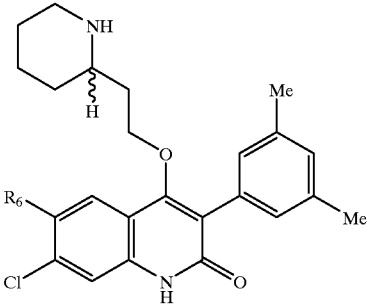

| Ex. # | $R_6$ | m/e |
|---|---|---|
| 1A | 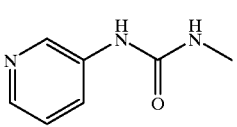 | 546 (M + H) |
| 1B | 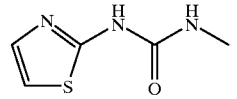 | 546 (M + H) |
| 1C | 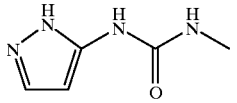 | 552 (M + H) |
| 1D | 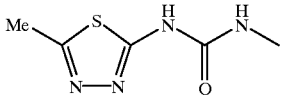 | 535 (M + H) |
| 1E | 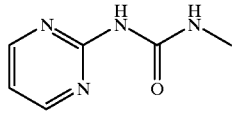 | 567 (M + H) |
| 1F | 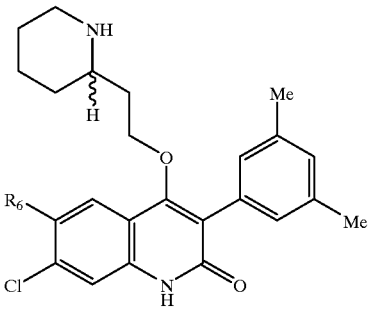 | 547 (M + H) |

-continued

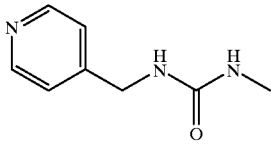

| Ex. # | $R_6$ | m/e |
|---|---|---|
| 1G | 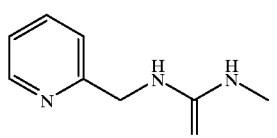 | 560 (M + H) |
| 1H | 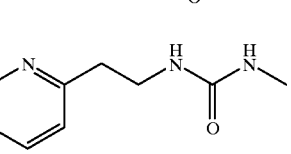 | 560 (M + H) |
| 1I | 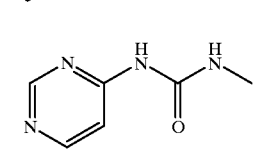 | 574 (M + H) |
| 1J | 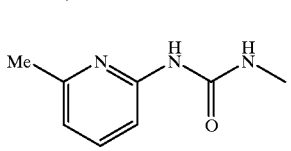 | 547 (M + H) |
| 1K | 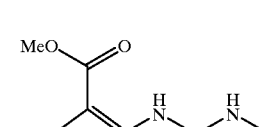 | 560 (M + H) |
| 1L | 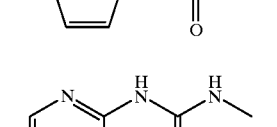 | 609 (M + H) |
| 1M | 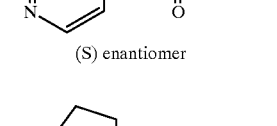 (S) enantiomer | 547 (M + H) |
| 1N | 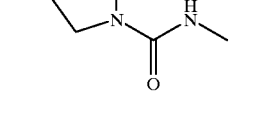 | 523 (M + H) |

-continued

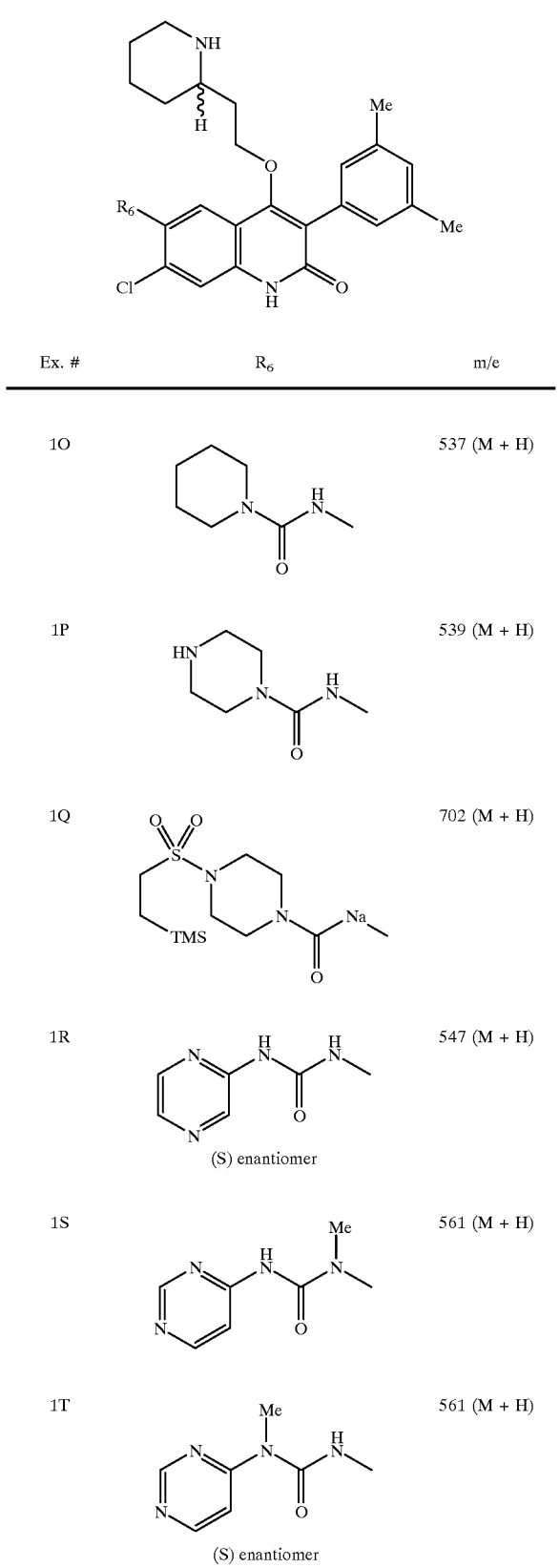

| Ex. # | R_6 | m/e |
|---|---|---|
| 1O | | 537 (M + H) |
| 1P | | 539 (M + H) |
| 1Q | | 702 (M + H) |
| 1R | (S) enantiomer | 547 (M + H) |
| 1S | (S) enantiomer | 561 (M + H) |
| 1T | (S) enantiomer | 561 (M + H) |

-continued

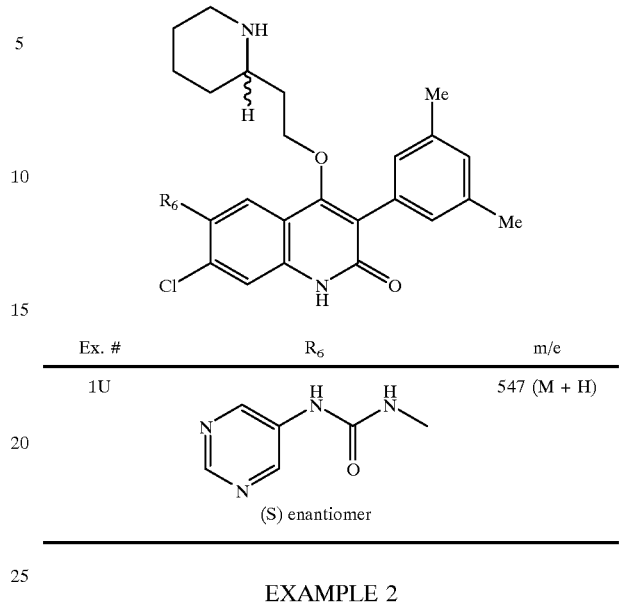

| Ex. # | R_6 | m/e |
|---|---|---|
| 1U | (S) enantiomer | 547 (M + H) |

EXAMPLE 2

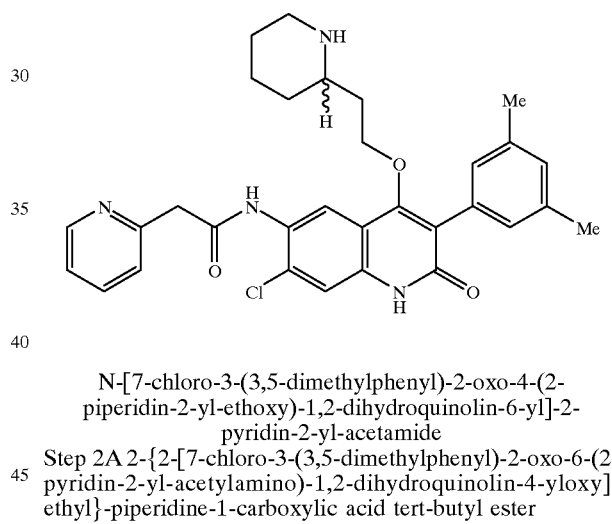

N-[7-chloro-3-(3,5-dimethylphenyl)-2-oxo-4-(2-piperidin-2-yl-ethoxy)-1,2-dihydroquinolin-6-yl]-2-pyridin-2-yl-acetamide Step 2A 2-{2-[7-chloro-3-(3,5-dimethylphenyl)-2-oxo-6-(2-pyridin-2-yl-acetylamino)-1,2-dihydroquinolin-4-yloxy]-ethyl}-piperidine-1-carboxylic acid tert-butyl ester To a suspension of pyridin-2-yl-acetic acid hydrochloride (60 mg in 0.8 mL methylene chloride) was added 0.051 mL triethylamine and the mixture stirred at room temperature for 10 minutes. At this time, 98 mg 1-(3-dimethylaminopropyl)-3-ethylcarbodiimide hydrochloride, 69 mg 1-hydroxybenzotriazole, and 60 mg 2-{2-[6-amino-7-chloro-3-(3,5-dimethylphenyl)-2-oxo-1,2-dihydro-quinolin-4-yloxy]-ethyl}-piperidine-1-carboxylic acid tert-butyl ester (prepared essentially as described in Example 1) were added in order. After 22 hours, the mixture was diluted with methylene chloride and extracted sequentially with water, 10% citric acid and brine. The organic portion was dried over sodium sulfate and the concentrate purified by flash chromatography on silica gel (hexane:ethyl acetate, 1:1; then methylene chloride:10% ammonium hydroxide in methanol, 95:5) to give the title compound, 55 mg.

Step 2B N-[7-chloro-3-(3,5-dimethylphenyl)-2-oxo-4-(2-piperidin-2-yl-ethoxy)-1,2-dihydroquinolin-6-yl]-2-pyridin-2-yl-acetamide To a solution of 2-{2-[7-chloro-3-(3,5-dimethylphenyl)-2-oxo-6-(2-pyridin-2-yl-acetylamino)-1,2-dihydroquinolin- 4-yloxy]-ethyl}-piperidine-1-carboxylic acid tert-butyl ester (55 mg in 4.0 mL methylene chloride) was added 2.0 mL trifluoroacetic acid and the mixture stirred at room temperature. After 20 minutes, the mixture was concentrated in vacuo, resolvated in 10% ammonium hydroxide in methanol and concentrated once again. Purification by flash chromatography on silica gel (methylene chloride:10% ammonium hydroxide in methanol, 95:5; then 90:10) gave the title compound, 40 mg.

Following a procedure similar to that described above, the following compounds were prepared:

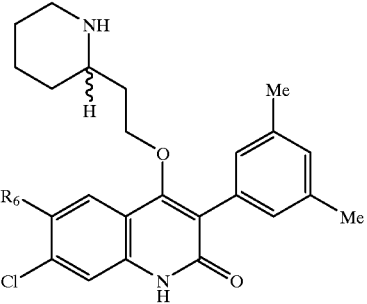

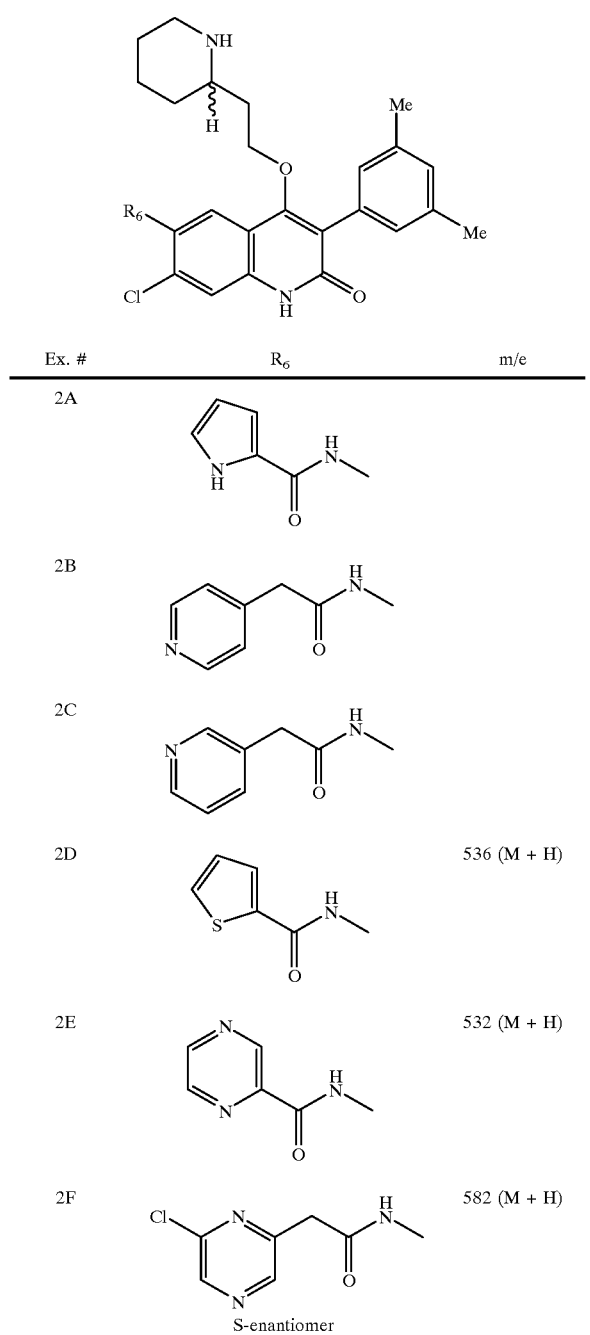

EXAMPLE 3.1

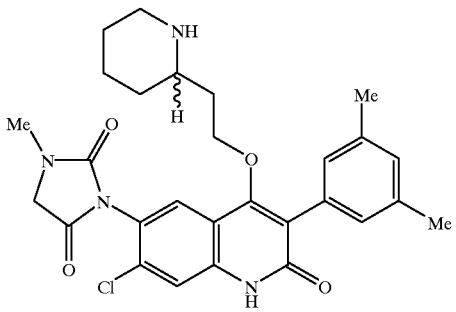

3-[7-chloro-3-(3,5-dimethylphenyl)-2-oxo-4-(2-piperidin-2-yl-ethoxy)-1,2-dihydroquinolin-6-yl]-1-methylimidazolidine-2,4-dione Step 3.1A 2-{2-[7-chloro-3-(3,5-dimethylphenyl)-6-nitro-2-oxo-1,2-dihydroquinolin-4-yloxy]-ethyl}-piperidine-1-carboxylic acid tert-butyl ester To a solution of 2-(2-hydroxyethyl)-piperidine-1-carboxylic acid tert-butyl ester (0.864 g in 38 mL dry tetrahydrofuran) was added 1.56 g of 7-chloro-3-(3,5-dimethylphenyl)-4-hydroxy-6-nitro-1H-quinolin-2-one followed by 1.19 g of triphenylphosphine and the mixture stirred at room temperature. To this was added 0.72 mL of diethyl azodicarboxylate (DEAD) and stirring was continued for 64 hours. At this time the solvents were removed in vacuo and the residue purified by flash chromatography on silica gel (hexane:ethyl acetate, 6:4) to give the title compound (1.56 g).

Step 3.1B 2-{2-[6-amino-7-chloro-3-(3,5-dimethylphenyl)-2-oxo-1,2-dihydroquinolin-4-yloxy]-ethyl}-1-piperidine-1-carboxylic acid tert-butyl ester To a solution of 2-{2-[7-chloro-3-(3,5-dimethylphenyl)-6-nitro-2-oxo-1,2-dihydroquinolin-4-yloxy]-ethyl}-piperidine-1-carboxylic acid tert-butyl ester (750 mg in 13 mL dry methanol) was added 18 mg iron(III)chloride hexahydrate followed by 100 mg activated carbon and the mixture heated to reflux on an oil bath. After 15 minutes, hydrazine (0.169 mL) was added dropwise and the reaction allowed to proceed at reflux for 12 hours. At this time, the mixture was cooled to room temperature, filtered through diatomaceous earth and the solvent removed in vacuo. The concentrate was solvated in 400 mL methylene chloride, washed successively with water (100 mL) and brine (100 mL), dried over sodium sulfate and concentrated in vacuo to give the title compound (crude: 710 mg).

Step 3.1C 2-{2-[7-chloro-3-(3,5-dimethylphenyl)-6-(3-methyl-2,5-dioxoimidazolidin-1-yl)-2-oxo-1,2-dihydroquinolin-4-yloxy]-ethyl}-piperidine-1-carboxylic acid tert-butyl ester To a solution of 2-{2-[6-amino-7-chloro-3-(3,5-dimethylphenyl)-2-oxo-1,2-dihydroquinolin-4-yloxy]-ethyl}-piperidine-1-carboxylic acid tert-butyl ester (53 mg in 2 mL dry methylene chloride) at 0° C. was added phosgene (0.077 mL of a 1.93 M solution in toluene) followed by 0.016 mL of pyridine and the mixture stirred for 1 hour at 0° C. At this time, 70 mg of sarcosine methyl ester hydrochloride was added and the mixture allowed to warm to room temperature. After 20 hours, the mixture was diluted with ethyl acetate (15 mL) and the reaction quenched by the addition of 10% citric acid. The organic portion was concentrated in vacuo to provide the crude title compound.

Step 3.1D 3-[7-chloro-3-(3,5-dimethylphenyl)-2-oxo-4-(2-piperidin-2-yl-ethoxy)-1,2-dihydroquinolin-6-yl]-1-methylimidazolidine-2,4-dione To a solution of 2-{2-[7-chloro-3-(3,5-dimethylphenyl)-6-(3-methyl-2,5-dioxoimidazolidin-1-yl)-2-oxo-1,2-dihydroquinolin-4-yloxy]-ethyl}-piperidine-1-carboxylic acid tert-butyl ester in 2.0 dry methylene chloride was added a few drops of anisole followed by 1.0 mL of trifluoroacetic acid and the mixture stirred at room temperature. After 1 hour the solvents were removed in vacuo and the resulting residue purified by flash chromatography on silica gel (methylene chloride:ammonium hydroxide:methanol, 96:1:3) to give the title compound.

EXAMPLE 3.2

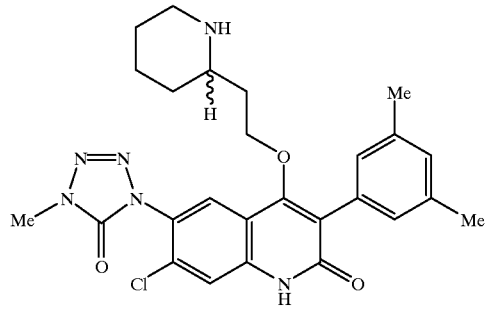

7-chloro-3-(3,5-dimethylphenyl)-6-(4-methyl-5-oxo-4,5-dihydro-tetrazol-1-yl)-4-(2-piperidin-2-yl-ethoxy)-1H-quinolin-2-one Step 3.2A 2-{2-[7-chloro-3-(3,5-dimethylphenyl)-6-nitro-2-oxo-1,2-dihydro-quinolin-4-yloxy]-ethyl}-piperidine-1-carboxylic acid 2-trimethylsilanylethyl ester To a solution of 7-chloro-3-(3,5-dimethylphenyl)-6-nitro-4-(2-piperidin-2-yl-ethoxy)-1H-quinolin-2-one (200 mg in 5 mL dicloroethane) was added 136 mg of 2-(trimethylsilyl) ethyl 4-nitrophenyl carbonate followed by 0.092 mL diisopropylethylamine and the mixture heated to reflux. After 20 hours, the reaction was cooled to room temperature, concentrated in vacuo and purified by flash chromatography on silica gel (ethyl acetate:hexane, 1:1) to give the title compound (183 mg.)

Step 3.2B 2-{2-[6-amino-7-chloro-3-(3,5-dimethylphenyl)-2-oxo-1,2-dihydroquinolin-4-yloxy]-ethyl}-piperidine-1-carboxylic acid 2-trimethylsilanylethyl ester Prepared essentially as described in EXAMPLE 3.1 StepB, starting from 2-{2-[7-chloro-3-(3,5-dimethylphenyl)-6-nitro-2-oxo-1,2-dihydro-quinolin-4-yloxy]-ethyl}-piperidine-1-carboxylic acid 2-trimethylsilanylethyl ester (183 mg) to give the title compound (173 mg).

Step 3.2C 2-{2-[7-chloro-3-(3,5-dimethylphenyl)-2-oxo-6-(5-oxo-4,5-dihydro-tetrazol-1-yl)-1,2-dihydro-quinolin-4-yloxy]-ethyl}-piperidine-1-carboxylic acid 2-trimethylsilanylethyl ester To a solution of 2-{2-[6-amino-7-chloro-3-(3,5-dimethylphenyl)-2-oxo-1,2-dihydroquinolin-4-yloxy]-ethyl}-piperidine-1-carboxylic acid 2-trimethylsilanylethyl ester (173 mg in 5 mL dry methylene chloride) at 0° C. was added triphosgene (36 mg) followed by 0.073 mL of pyridine and the mixture stirred for 2 hour at 0° C. At this time the reaction was quenched by the addition water, washed with brine, dried over sodium sulfate and concentrated in vacuo to give the crude isocyante. This was solvated in 2 mL methylene chloride and added by cannula to a freshly prepared solution of aluminum azide (0.6 mmols in 5 mL tetrahydrofuran) and the resulting mixture heated to reflux on an oil bath. After 20 hours, the mixture was added to 10 mL of an iced, 1M potassium tartarate solution and stirred for 20 minutes. This was then diluted with water and extracted with ethyl acetate. The organic portion was washed successively with 1 M potassium tartarate, saturated ammonium chloride, water and brine, then dried over sodium sulfate. Purification of the concentrate by flash chromatography on silica gel (chloroform:10% acetic acid in methanol, 97:3) gave the title compound (160 mg).

Step 3.2D 2-{2-[7-chloro-3-(3,5-dimethylphenyl)-6-(4-methyl-5-oxo-4,5-dihydro-tetrazol-1-yl)-2-oxo-1,2-dihydro-quinolin-4-yloxy]-ethyl}-piperidine-1-carboxylic acid 2-trimethylsilanylethyl ester To a solution of 2-{2-[7-chloro-3-(3,5-dimethylphenyl)-2-oxo-6-(5-oxo-4,5-dihydro-tetrazol-1-yl) -1,2-dihydro-quinolin-4-yloxy]-ethyl}-piperidine-1-carboxylic acid 2-trimethylsilanylethyl ester (35 mg in 2 mL dry N,N-dimethylformamide) was added 26 mg of finely powdered potassium carbonate followed by 0.011 mL iodomethane and the mixture stirred at room temperature. After 30 minutes, the reaction was quenched by the addition of saturated ammonium chloride and the mixture partitioned between ethyl acetate and water. The organic layer was isolated and washed with water and brine, then dried over sodium sulfate. Purification of the concentrate by preparative tlc on silica gel (hexane:ethyl acetate, 3:2) gave the title compound (21 mg).

Step 3.2E 7-chloro-3-(3,5-dimethylphenyl)-6-(4-methyl-5-oxo-4,5-dihydro-tetrazol-1-yl)-4-(2-piperidin-2-yl-ethoxy)-1H-quinolin-2-one Prepared essentially as described in EXAMPLE 3.1, Step D starting from 2-{2-[7-chloro-3-(3,5-dimethylphenyl)-6-(4-methyl-5-oxo-4,5 -dihydro-tetrazol-1-yl)-2-oxo-1,2-dihydro-quinolin-4-yloxy]-ethyl}-piperidine-1-carboxylic acid 2-trimethylsilanylethyl ester (21 mg) to give the title compound (15 mg). MASS: 509 (M+H)

EXAMPLE 3.3

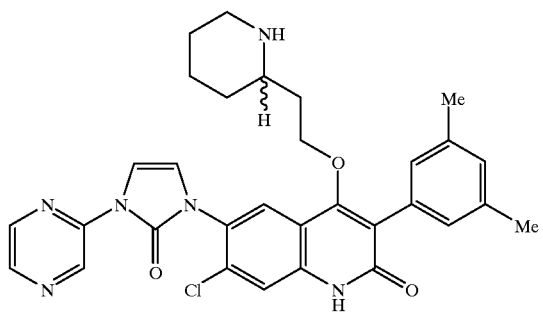

7-chloro-3-(3,5-dimethylphenyl)-6-(2-oxo-3-pyrazin-2-yl-2,3-dihydro-imidazol-1-yl)-4-(2-piperidin-2-yl-ethoxy)-1H-quinolin-2-one Step 3.3A 2-{2-[7-chloro-3-(3,5-dimethylphenyl)-6-isocyanato-2-oxo-1,2-dihydroquinolin-4-yloxy]-ethyl}-piperidine-1-carboxylic acid 2-trimethylsilanyl-ethyl ester To a solution of 2-{2-[6-amino-7-chloro-3-(3,5-dimethylphenyl)-2-oxo-1,2-dihydroquinolin-4-yloxy]-ethyl}-piperidine-1-carboxylic acid 2-trimethylsilanylethyl ester (from EXAMPLE 3.2B, 90 mg in a mixture of 1 mL chloroform and 1 mL water containing 47 mg calcium carbonate) at 0° C. was added 46 mg triphosgene and the mixture allowed to warm slowly to room temperature. After 2 hours, the reaction was quenched by the addition of 2N hydrochloric acid, extracted with methylene chloride and the organics dried over sodium sulfate to give the crude title compound (94 mg).

Step 3.3B 2-{2-[7-chloro-6-[3-(2,2-dimethoxyethyl)-3-pyrazin-2-yl-ureido]-3-(3,5 -dimethylphenyl)-2-oxo-1,2-dihydroquinolin-4-yloxy]-ethyl}-piperidine-1-carboxylic acid 2-trimethylsilanylethyl ester To a solution of (2,2-dimethoxyethyl)-pyrazin-2-yl-amine (103 mg in 3 mL dry tetrahydrofuran) at −78° C. was added 0.23 mL of a 2.5M solution of butyllithium and the mixture stirred for 30 minutes. At this time, a solution of 2-{2-[7-chloro-3-(3,5-dimethylphenyl)-6-isocyanato-2-oxo-1,2-dihydroquinolin-4-yloxy]-ethyl}-piperidine-1-carboxylic acid 2-trimethylsilanylethyl ester (94 mg in 2 mL tetrahydrofuran) was added via cannula and the mixture warmed to room temperature. After 20 hours, the reaction was quenched by the addition of saturated ammonium chloride and extracted with chloroform. The organic portion was washed with brine, dried over sodium sulfate and concentrated in vacuo. Purification of the residue by preparative tlc on silica gel (ethyl acetate) gave the title compound (11 mg).

Step 3.3C 7-chloro-3-(3.5-dimethylphenyl)-6-(2-oxo-3-pyrazin-2-yl-2,3-dihydro-imidazol-1-yl)-4-(2-piperidin-2-yl-ethoxy)-1H-quinolin-2-one To a solution of 2-{2-[7-chloro-6-[3-(2,2-dimethoxyethyl)-3-pyrazin-2-yl-ureido]-3-(3,5-dimethylphenyl)-2-oxo-1,2-dihydroquinolin-4-yloxy]-ethyl}-piperidine-1-carboxylic acid 2-trimethylsilanylethyl ester (11 mg in 2 mL chloroform) was added aqueous trifluoroacetic acid and the mixture heated to reflux on an oil bath. After 8 hours, the reaction mixture was concentrated in vacuo and the residue purified by preparative tic on silica gel (chloroform:methanol, 9:1) to give the title compound (4.7 mg). MASS: 571 (M+H)

PREPARATION OF SYNTHETIC INTERMEDIATES (2,2-dimethoxyethyl)-pyrazin-2-yl-amine

To a solution of 2-chloropiperazine (1.0 g in 5 mL dry toluene) was added 2,2-dimethoxyethylamine (1.1 g) followed by 1.2 mL triethylamine and the mixture heated to reflux on an oil bath. After 48 hours, the reaction mixture was applied to a flash chromatography column (silica gel) for purification (ethyl acetate:hexane, 7:3; then 100:0) to give the title compound (101 mg).

EXAMPLE 3.4

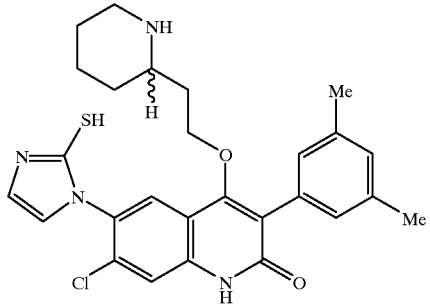

7-chloro-3-(3,5-dimethylphenyl)-6-(2-methylsulfanylimidazol-1-yl)-4-(2-piperidin-2-yl-ethoxy)-1H-quinolin-2-one Step 3.4A 2-{2-[7-chloro-3-(3,5-dimethylphenyl)-6-isothiocyanato-2-oxo-1,2-dihydroquinolin-4-yloxy]-ethyl}-piperidine-1-carboxylic acid tert-butyl ester To a stirred suspension of calcium carbonate (320 mg) and thiophosgene (120 mg) in 10 mL water:chloroform (1:1) at 0° C. was added 2-{2-[6-amino-7-chloro-3-(3,5-dimethylphenyl)-2-oxo-1,2-dihydro-quinolin-4-yloxy]-ethyl}-piperidine-1-carboxylic acid tert-butyl ester (450 mg, prepared essentially as described in Example 1) and the mixture stirred at low temperature. After 2 hours the reaction was quenched by the addition of 10% hydrochloric acid and stirring continued until the gas evolution ceased. The mixture was then extracted with chloroform, the combined organics dried over magnesium sulfate and concentrated in vacuo to provide the crude title compound (480 mg).

Step 3.4B 2-(2-{7-chloro-3-(3,5-dimethylphenyl)-6-[3-(2-ethoxy-3-methoxypropyl)-thioureido]-2-oxo-1,2-dihydro-quinolin-4-yloxy}-ethyl)-piperidine-1-carboxylic acid tert-butyl ester To a solution of 2-{2-[7-chloro-3-(3,5-dimethylphenyl)-6-isothiocyanato-2-oxo-1,2-dihydroquinolin-4-yloxy]-ethyl}-piperidine-1-carboxylic acid tert-butyl ester (480 mg in 15 mL dry toluene) was added 130 mg of 2,2-diethoxy-ethylamine and the mixture stirred at room temperature for 30 minutes, then heated to reflux on an oil bath. After 2 hours the mixture was cooled to room temperature, concentrated in vacuo and the residue washed with diethyl ether. Collection of the solids gave the crude title compound (410 mg).

Step 3.4C 7-chloro-3-(3.5-dimethylphenyl)-6-(2-methylsulfanylimidazol-1-yl)-4-(2-piperidin-2-yl-ethoxy)-1H-quinolin-2-one A solution of 2-(2-{7-chloro-3-(3,5-dimethylphenyl)-6-[3-(2-ethoxy-3-methoxypropyl)-thioureido]-2-oxo-1,2-dihydro-quinolin-4-yloxy}-ethyl)-piperidine-1-carboxylic acid tert-butyl ester (410 mg in 20 mL 30% sulfuric acid) was heated to reflux on an oil bath. After 20 hours, the reaction was cooled to room temperature and washed with methylene chloride. The aqueous portion was neutralized by the addition of sodium hydroxide and the mixture then concentrated in vacuo. Purification of the residue by flash chromatography on silica gel (ethyl acetate; then chloroform:1% ammonia in methanol, 9:1) gave the title compound (150 mg).

Following a procedure similar to that described above, the following compounds were prepared:

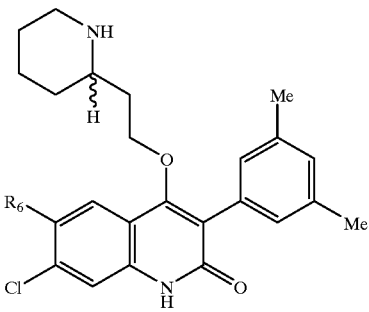

| Ex. # | $R_6$ | m/e |
|---|---|---|
| 3A | (5-methyl-2,4-dioxoimidazolidin-1-yl, methyl) | 523 (M + H) |
| 3B | (1-methyl-2,4-dioxo-1,3-diazaspiro[4.2]heptane) | 535 (M + H) |
| 3C | (3-methyl-thieno[3,2-d]pyrimidine-2,4-dione) | 577 (M + H) |
| 3D | (1-cyclopropyl-3-methyl-imidazolidin-2-one) | 535 (M + H) |
| 3E | (4-methyl-5-oxo-tetrazole) | 495 (M + H) |
| 3F | (1-ethyl-4-methyl-5-oxo-tetrazole) | 523 (M + H) |
| 3G | (1-propyl-4-methyl-5-oxo-tetrazole) | 537 (M + H) |
| 3H | (1-butyl-4-methyl-5-oxo-tetrazole) | 551 (M + H) |

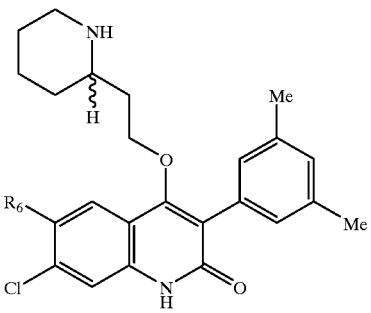

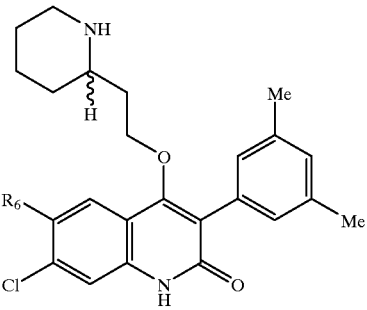

| Ex. # | R₆ | m/e |
|---|---|---|
| 3I | (tetrazolone with isobutyl and Me substituents, Me shown) | 551 (M + H) |
| 3J | (tetrazolone with isopropyl and Me substituents) | 537 (M + H) |
| 3K | (tetrazolone with benzyl and Me substituents) | 585 (M + H) |
| 3L | (tetrazolone with pyrimidinylmethyl and Me substituents) | 587 (M + H) |

EXAMPLE 4.1

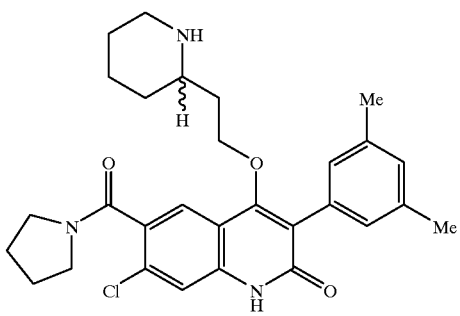

7-chloro-3-(3,5-dimethylphenyl)-4-(2-piperidin-2-yl-ethoxy)-6-(pyrrolidine-1-carbonyl)-1H-quinolin-2-one Step 4.1A 2-amino-4-chloro-5-iodobenzoic acid methyl ester To a suspension of 2-acetylamino-4-chlorobenzoic acid methyl ester (2.0 g in 80 mL of dry chloroform) and 2.5 g silver trifluoromethanesulfonate was added iodine (2.87 g in 40 mL chloroform) and the mixture stirred at room temperature. After 5 hours, the mixture was filtered over diatomaceous earth and the filtrate concentrated in vacuo. Purification of the resulting oil by flash chromatography on silica gel (hexane:ethyl acetate, 95:5; then 90:10) gave the title compound (2.26 g).

Step 4.1B 4-chloro-2-[2-(3,5-dimethylphenyl)-acetylamino]-5-iodo-benzoic acid methyl ester To a solution of 2-amino-4-chloro-5-iodobenzoic acid methyl ester (2.26 g in 25 mL dichloroethane) was added (3,5-dimethylphenyl) acetyl chloride (1.2 g in 15 mL dichloroethane) and the mixture heated to 75° C. on an oil bath. After 3 hours, the reaction was cooled and the solvent removed in vacuo. The title compound was isolated by crystallization from methanol (2.7 g).

Step 4.1C 5-allyl-4-chloro-2-[2-(3,5-dimethylphenyl)-acetylamino]-benzoic acid methyl ester To a suspension of 4-chloro-2-[2-(3,5-dimethylphenyl)-acetylamino]-5-iodo-benzoic acid methyl ester (2.39 g in 12 mL N,N-dimethylformamide) and 0.183 g bis(triphenylphosphine)palladium(II) chloride was added 2.02 mL allyltin and the mixture heated to 100° C. on an oil bath. After 2 hours, the mixture was cooled, partitioned between ethyl acetate and water and the organic layer washed further with brine. Concentration of the dried (magnesium sulfate) organics and purification by flash chromatography on silica gel (hexane:ethyl acetate, 95:5; then 90:10) gave the title compound (1.4 g).

Step 4.1D 6-allyl-7-chloro-3-(3 5-dimethylphenyl)-4-hydroxy-1H-quinolin-2-one

To a solution of 5-allyl-4-chloro-2-[2-(3,5-dimethylphenyl)-acetylamino]-benzoic acid methyl ester (1.4 g in 40 mL dry tetrahydrofuran) at 0° C. was added dropwise a solution of sodium bis(trimethylsilyl)amide (9.8 mL of a 1.0M solution in tetrahydrofuran) and the mixture warmed to room temperature. After 4 hours, the reaction was cooled to 0° C. and quenched by the addition of of 200 mL iced 6N hydrochloric acid. The slurry was stirred for 15 minutes then filtered and washed sequentially with ice water (500 mL), cold hexane (200 mL) and cold toluene (100 mL). The residue was dried in vacuo to give the title compound (960 mg).

Step 4.1E 2-{2-[6-allyl-7-chloro-3-(3,5-dimethylphenyl)-2-oxo-1,2-dihydroquinolin-4-yloxy]-ethyl}-piperidine-1-carboxylic acid tert-butyl ester To a solution of 6-allyl-7-chloro-3-(3,5-dimethylphenyl)-4-hydroxy-1H-quinolin-2-one (960 mg in 30 mL of tetrahydrofuran) at 0° C. was added 615 mg of 2-(2-hydroxyethyl)-piperidine-1-carboxylic acid tert-butyl ester and 1.04 g of triphenylphosphine followed by 0.56 mL of diethyl azodicarboxylate and the mixture warmed to room temperature. After 20 hours, the solvents were removed in vacuo and the residue purified by flash chromatography on silica gel (hexane:ethylacetate, 85:15; then 80:20; then 90:10) to give the title compound (1.19 g).

Step 4.1F 4-[2-(1-tert-butoxycarbonyl-piperidin-2-yl)-ethoxy]-7-chloro-3-(3,5-dimethylphenyl)-2-oxo-1,2-dihydro-quinoline-6-carboxylic acid To a solution of 2-{2-[6-allyl-7-chloro-3-(3,5-dimethylphenyl)-2-oxo-1,2-dihydroquinolin-4-yloxy]-ethyl}-piperidine-1-carboxylic acid tert-butyl ester (517 mg in 35 mL of a mixture of tert-butanol:tetrahydrofuran:water, 10:3:1) was added 121 mg 4-methylmorpholine N-oxide and 48 mg osmium tetraoxide and the mixture stirred at room temperature. After 2 hours, the reaction was diluted with 7.5 mL of water followed by the addition sodium periodate (602 mg) and sodium bicarbonate (946 mg) and the resulting suspension stirred rapidly for 90 minutes. The mixture was then filtered over diatomaceous earth and extracted with ethyl acetate. Concentration of the organics in vacuo provided the crude aldehyde product which was used in the following reaction without purification.

The crude product was solvated in 15 mL tert-butanol followed by the addition of sodium phosphate (8 mL of a 1.25 M aqueous solution) and potassium permanganate (15 mL of a 1 M aqueous solution) and the mixture stirred at room temperature. After 2 hours, the reaction was quenched by the addition of sodium sulfite, extracted with ethyl acetate, and the aqueous layer adjusted to pH3 with 1 N hydrochloric acid. The aqueous portion was extracted with ethyl acetate and the organics dried over magnesium sulfate. Purification of the concentrate by flash chromatography on silica gel (hexane:ethyl acetate, 7:3+1% acetic acid) provided the title compound (150 mg).

Step 4.1G 2-{2-[7-chloro-3-(3,5-dimethylphenyl)-2-oxo-6-(pyrrolidine-1-carbonyl)-1,2-dihydroquinolin-4-yloxy]-ethyl}-piperidine-1-carboxylic acid tert-butyl ester To a solution of 4-[2-(1-tert-butoxycarbonyl-piperidin-2-yl)-ethoxy]-7-chloro-3-(3,5-dimethylphenyl)-2-oxo-1,2-dihydro-quinoline-6-carboxylic acid (15 mg in 0.6 mL of dry methylene chloride) was added 8.0 mg of 1-(3-dimethylaminopropyl)-3-ethylcarbodiimide hydrochloride (EDC) followed by 6.0 mg 1-hydroxybenzotriazole (HOBt) and the mixture stirred for 10 minutes. At this time, 9.4 mg of pyrrolidine and the reaction allowed to proceed at room temperature. After 4 hours, the mixture was concentrated in vacuo and purified by flash chromatography on silica gel (methylene chloride:10% ammonium hydroxide in methanol, 95:5) to give the tilte compound (8 mg).

Step 4.1H 7-chloro-3-(3.5-dimethylphenyl)-4-(2-piperidin-2-yl-ethoxy)-6-(pyrrolidine-1-carbonyl)-1H-quinolin-2-one To a solution of 2-{2-[7-chloro-3-(3,5-dimethylphenyl)-2-oxo-6-(pyrrolidine-1-carbonyl)-1,2-dihydroquinolin-4-yloxy]-ethyl}-piperidine-1-carboxylic acid tert-butyl ester (8.0 mg in 2.0 dry methylene chloride) was added a few drops of anisole followed by 1.0 mL of trifluoroacetic acid and the mixture stirred at room temperature. After 30 minutes the solvents were removed in vacuo and the resulting residue purified by flash chromatography on silica gel (methylene chloride: 10% ammonium hydroxide in methanol, 95:5; then 90:10) to give the title compound (5 mg).

EXAMPLE 4.2

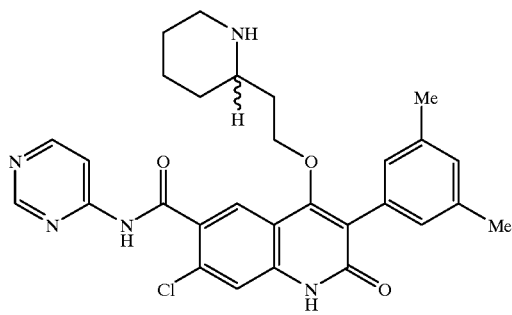

7-chloro-3-(3,5-dimethylphenyl)-2-oxo-4-(2-piperidin-2-yl-ethoxy)-1,2-dihydroquinoline-6-carboxylic acid pyrimidin-4-ylamide Step 4.2A 7-chloro-3-(3,5-dimethylphenyl)-4-hydroxy-6-iodo-1H-quinolin-2-one To a solution of 4-chloro-2-[2-(3,5-dimethylphenyl)-acetylamino]-5-iodo-benzoic acid methyl ester (EXAMPLE 4.1B, 10.9 g in 180 mL dry tetrahydrofuran) at 0° C. was added dropwise 59.5 mL of a 1 M solution of sodium bis(trimethylsilyl)amide in tetrahydrofuran and the mixture allowed to warm to room temperature. After 1.5 hours, the mixture was cooled to 0° C. and the reaction quenched by the addition of 400 mL ice:6N hydrochloric acid (1:1). This was stirred for 15 minutes then filtered to collect the solid product. The solids were washed with ice-water then cold acetonitrile and dried to give the title compound (9.8 g).

Step 4.2B 2-{2-[7-chloro-3-(3.5-dimethylphenyl)-6-iodo-2-oxo-1,2-dihydroquinolin-4-yloxy]-ethyl}-piperidine-1-carboxylic acid tert-butyl ester To a solution of 2-(2-hydroxyethyl)-piperidine-1-carboxylic acid tert-butyl ester (10 g in 450 mL dry tetrahydrofuran) was added 22.3 g of 7-chloro-3-(3,5-dimethylphenyl)-4-hydroxy-6-iodo-1H-quinolin-2-one followed by 13.7 g of triphenylphosphine and the mixture stirred at room temperature. To this was added 8.2 mL of diethyl azodicarboxylate (DEAD) and stirring was continued for 72 hours. At this time the solvents were removed to a minimum volume in vacuo and the mixture filterd through a silica gel pad to remove the phosphine by-products. The filtrate was concentrated in vacuo to provide the partially purified title compound (17.5 g).

Step 4.2C 2-{2-[7-chloro-3-(3,5-dimethylphenyl)-2-oxo-6-(pyrimidin-4-ylcarbamoyl)-1,2-dihydroquinolin-4-yloxy]-ethyl}-piperidine-1-carboxylic acid tert-butyl ester To a suspension of 2-{2-[7-chloro-3-(3,5-dimethylphenyl)-6-iodo-2-oxo -1,2-dihydroquinolin-4-yloxy]-ethyl}-piperidine-1-carboxylic acid tert-butyl ester (0.10 g in a mixture of 1 mL N,N-dimethylformamide and 0.04 mL triethylamine) was added 75 mg of 4-aminopyrimidine followed by 0.8 mg dichlorobis(triphenylphosphine)palladium(II) and the flask flushed (5×) with carbon monoxide. The mixture was then heated to 90° C. on an oil bath under a carbon monoxide atmosphere. After 16 hours, the mixture was cooled to room temperature, diluted with ethyl acetate and washed with water and brine. The organic portion was dried over sodium sulfate and concentrated in vacuo. Purification by flash chromatography on silica gel (ethyl acetate:hexane, 35:65; then methylene chloride:methanol, 95:5) gave the title compound (70 mg).

Step 4.2D 7-chloro-3-(3,5-dimethylphenyl)-2-oxo-4-(2-piperidin-2-yl-ethoxy)-1,2-dihydroquinoline-6-carboxylic acid pyrimidin-4-ylamide Prepared essentially as described in EXAMPLE 5, Step B from 2-{2-[7 -chloro-3-(3,5-dimethylphenyl)-2-oxo-6-(pyrimidin-4-ylcarbamoyl)-1,2-dihydroquinolin-4-yloxy]-ethyl}-piperidine-1-carboxylic acid tert-butyl ester. MASS: 532 (M+H)

Following a procedure similar to that described above, the following compounds were prepared:

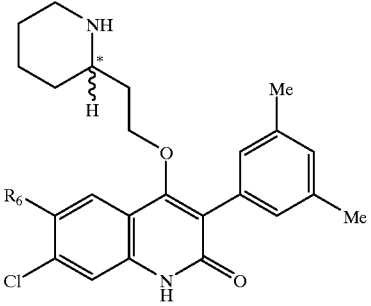

-continued

[Structure: piperidine-CH(*)-H-CH2-O-quinolin-2(1H)-one with 3-(3,5-dimethylphenyl), 6-R6, 7-Cl substituents]

| Ex. # | R6 | m/e |
|---|---|---|
| 4R | 1,3,4-thiadiazol-2-yl-NHC(O)- | 538 (M + H) |
| 4S | 2,6-dimethylpyrimidin-4-yl-NHC(O)- | 560 (M + H) |
| 4T | 1,2,5-thiadiazol-3-yl-NHC(O)- *S-enantiomer | 538 (M + H) |
| 4U | 1-ethyl-pyrazol-5-yl-NHC(O)- | 548 (M + H) |
| 4V | 2-methoxypyrimidin-4-yl-NHC(O)- *S-enantiomer | |
| 4W | 6-chloropyrimidin-4-yl-NHC(O)- *S-enantiomer | 566 (M + H) |
| 4X | 2-methylpyrimidin-4-yl-NHC(O)- *S-enantiomer | 546 (M + H) |
| 4Y | 5-methylpyrimidin-4-yl-NHC(O)- *S-enantiomer | 546 (M + H) |

-continued

[Same core structure]

| Ex. # | R6 | m/e |
|---|---|---|
| 4Z | 5-cyanopyrimidin-4-yl-NHC(O)- *S-enantiomer | 557 (M + H) |
| 4AA | pyrimidin-4-yl-N(Me)C(O)- | |
| 4BB | 2-cyclopropylpyrimidin-4-yl-NHC(O)- *S-enantiomer | 572 (M + H) |
| 4CC | 2-(1-adamantyl)pyrimidin-4-yl-NHC(O)- *S-enantiomer | 666 (M + H) |
| 4DD | azabicyclic-N-C(O)- *S-enantiomer | 534 (M + H) |
| 4EE | 2-phenylpyrimidin-4-yl-NHC(O)- *S-enantiomer | 608 (M + H) |

-continued

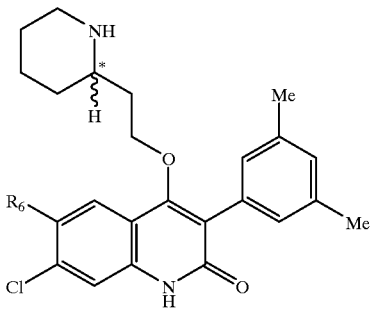

| Ex. # | R₆ | m/e |
|---|---|---|
| 4FF | 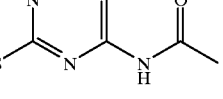 | |
| 4GG | 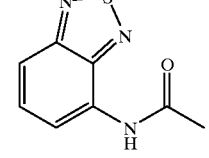 | |
| 4HH | 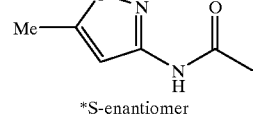  *S-enantiomer | 535 (M + H) |
| 4II | 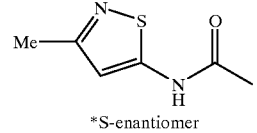  *S-enantiomer | 551 (M + H) |
| 4JJ | 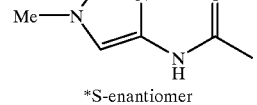  *S-enantiomer | 534 (M + H) |
| 4KK | 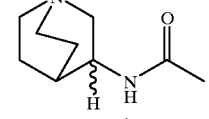  *S-enantiomer | |
| 4LL | 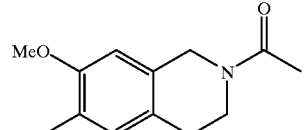  *S-enantiomer | 630 (M + H) |

-continued

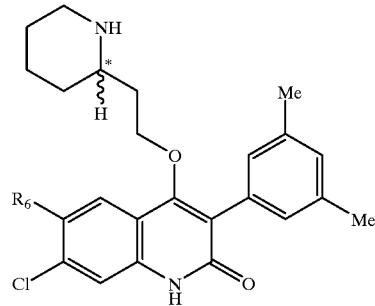

| Ex. # | R₆ | m/e |
|---|---|---|
| 4MM | 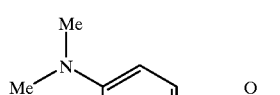  *S-enantiomer | 574 (M + H) |
| 4NN | 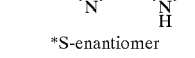  *S-enantiomer | 537 (M + H) |

EXAMPLE 5

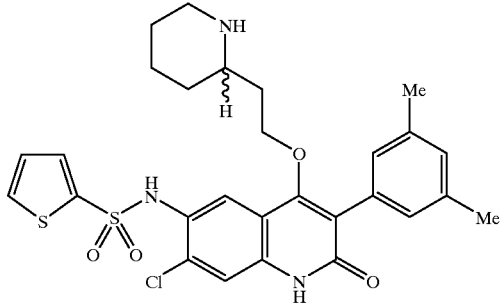

Thiophene-2-sulfonic acid [7-chloro-3-(3,5-dimethylphenyl)-2-oxo-4-(2-piperidin-2-yl-ethoxy)-1,2-dihydroquinolin-6-yl]-amide Step 5A 2-{2-[7-chloro-3-(3,5-dimethylphenyl)-2-oxo-6-(thiophene-2-sulfonylamino)-1,2-dihydroquinolin-4-yloxy]-ethyl}-piperidine-1-carboxylic acid tert-butyl ester To a solution of 2-{2-[6-amino-7-chloro-3-(3,5-dimethylphenyl)-2-oxo-1,2-dihydro-quinolin-4-yloxy]-ethyl}-piperidine-1-carboxylic acid tert-butyl ester (prepared essentially as described in Example 1, 200 mg in 10 mL pyridine) was added a catalytic amount of N,N-dimethylaminopyridine followed by 139 mg 2-thiophenesulfonyl chloride and the mixture stirred at room temperature. After 30 minutes, the reaction was quenched by the addition of saturated aqueous sodium bicarbonate, extracted with ethyl acetate and dried over sodium sulfate. Concentration in vacuo gave the crude title compound.

Step 5B Thiophene-2-sulfonic acid [7-chloro-3-(3,5-dimethylphenyl)-2-oxo-4-(2-piperidin-2-yl-ethoxy)-1,2-dihydroquinolin-6-yl]-amide To a solution of 2-{2-[7-chloro-3-(3,5-dimethylphenyl)-2-oxo-6-(thiophene-2-sulfonylamino)-1,2-dihydroquinolin-4-yloxy]-ethyl}-piperidine-1-carboxylic acid tert-butyl ester in 5 mL methylene chloride was added a few drops of anisole followed by 1.0 mL of trifluoroacetic acid and the mixture stirred at room temperature. After 30 minutes the solvents were removed in vacuo and the resulting residue purified by flash chromatography on silica gel (methylene chloride:10% ammonium hydroxide in methanol, 95:5; then 90:10) to give the title compound.

EXAMPLE 6.1

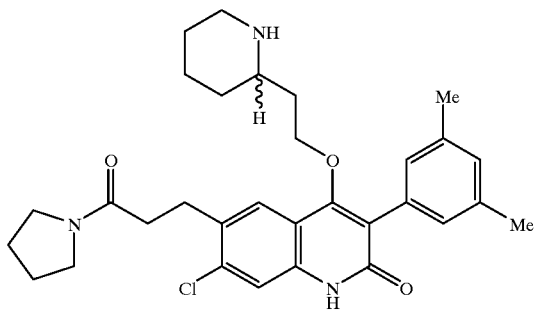

7-chloro-3-(3,5-dimethylphenyl)-6-(3-oxo-3-pyrrolidin- 1 -yl-propyl)-4-(2-piperidin-2-yl-ethoxy)-1H-quinolin-2-one Step 6.1A 2-{2-[7-chloro-3-(3,5-dimethylphenyl)-6-(3-hydroxy-propyl)-2-oxo-1,2-dihydroquinolin-4-yloxy]-ethyl}-piperidine-1-carboxylic acid tert-butyl ester To a solution of 2-{2-[6-allyl-7-chloro-3-(3,5-dimethylphenyl)-2-oxo-1,2-dihydroquinolin-4-yloxy]-ethyl}-piperidine-1-carboxylic acid tert-butyl ester (Example 4, Step 4E: 400 mg in 7.0 mL of dry tetrahydrofuran) at 0° C. was added 2.18 mL of a 1M solution of borane in tetrahydrofuran dropwise over 10 minutes. After 3 hours, the reaction was treated sequentially with sodium hydroxide (0.84 mL of a 3M solution) and hydrogen peroxide (0.29 mL of a 30% solution) and the mixture allowed to warm to room temperature. After 2 hours the mixture was extracted with ethyl acetate, washed with brine and dried over sodium sulfate. Purification of the concentrate by flash chromatography on silica gel (hexane:ethyl acetate, 8:2; then 7:3; then 3:2; then 1:1) gave the title compound (253 mg).

Step 6.1B 2-{2-[6-(2-carboxyethyl)-7-chloro-3-(3 5-dimethylphenyl)-2-oxo-1,2-dihydroquinolin-4-yloxy]-ethyl}-piperidine-1-carboxylic acid tert-butyl ester To a solution of 2-{2-[7-chloro-3-(3,5-dimethylphenyl)-6-(3-hydroxy-propyl)-2-oxo-1,2-dihydroquinolin-4-yloxy]-ethyl}-piperidine-1-carboxylic acid tert-butyl ester (176 mg in 3.0 mL methylene chloride) was added 20 mg powdered 4Å sieves, 73 mg of 4-methylmorpholine-N-oxide, followed by 11 mg tetrapropylammonium perruthenate(VII) and the mixture stirred at room temperature. After 3 hours, the solvent was removed in vacuo and the crude aldehyde product resolvated in a mixture of tert-butanol (2 mL) and sodium phosphate (1 mL of a 1.25M solution). To this was added 1.86 mL of a 1M aqueous solution of potassium permanganate. After 30 minutes, the mixture was extracted with ethyl acetate, dried over sodium sulfate and purified by flash chromatography on silica gel (hexane:ethyl acetate, 1:1; then methylene chloride:methanol, 90:10) to give the title compound (107 mg).

Step 6.1C 2-{2-[7-chloro-3-(3,5-dimethylphenyl)-2-oxo-6-(3-oxo-3-pyrrolidin-1-yl-propyl)-1,2-dihydroquinolin-4-yloxy]-ethyl}-piperidine-1-carboxylic acid tert-butyl ester To a solution of 2-{2-[6-(2-carboxyethyl)-7-chloro-3-(3, 5-dimethylphenyl)-2-oxo-1,2-dihydroquinolin-4-yloxy]-ethyl}-piperidine-1-carboxylic acid tert-butyl ester (15 mg in 0.5 mL of dry methylene chloride) was added 8.0 mg of 1-(3-dimethylaminopropyl)-3-ethylcarbodiimide hydrochloride (EDC) followed by 5.2 mg 1-hydroxybenzotriazole (HOBt) and the mixture stirred for 10 minutes. At this time, 9.2 mg of pyrrolidine was added and the reaction allowed to proceed at room temperature. After 40 minutes, the mixture was concentrated in vacuo and purified by flash chromatography on silica gel (methylene chloride: 10% ammonium hydroxide in methanol, 95:5; then 90:10) to give the title compound (9 mg).

Step 6.1D 7-chloro-3-(3,5-dimethylphenyl)-6-(3-oxo-3-pyrrolidin-1-yl-propyl)-4-(2-piperidin-2-yl-ethoxy)-1H-quinolin-2-one To a solution of 2-{2-[7-chloro-3-(3,5-dimethylphenyl)-2-oxo-6-(3-oxo-3-pyrrolidin-1-yl-propyl)-1,2-dihydroquinolin-4-yloxy]-ethyl}-piperidine-1-carboxylic acid tert-butyl ester (9.0 mg in 2.0 dry methylene chloride) was added a few drops of anisole followed by 1.0 mL of trifluoroacetic acid and the mixture stirred at room temperature. After 30 minutes the solvents were removed in vacuo and the resulting residue purified by flash chromatography on silica gel (methylene chloride:10% ammonium hydroxide in methanol, 9:1) to give the title compound (7.0 mg). MASS: 536 (M+H)

EXAMPLE 6.2

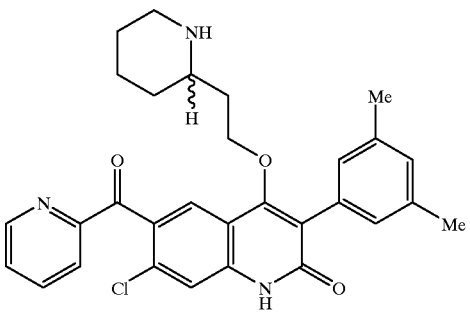

7-chloro-3-(3,5 -dimethylphenyl)-4-(2-piperidin-2-yl-ethoxy)-6 (pyridine-2-carbonyl)- 1H-quinolin-2-one Step 6.2A 2-{2-[7-chloro-3-(3,5-dimethylphenyl)-2-oxo-6-(pyridine-2-carbonyl)-1,2-dihydroquinolin-4-yloxy]-ethyl}-piperidine-1-carboxylic acid tert-butyl ester To a solution of 2-{2-[7-chloro-3-(3,5-dimethylphenyl)-6-iodo-2-oxo-1,2-dihydroquinolin-4-yloxy]-ethyl}-piperidine-1-carboxylic acid tert-butyl ester (78 mg in 1 mL N,N-dimetlylformamide) was added 0.045 mg 2-tributylstannanyl-pyridine followed by 0.03 mL triethylamine and 0.002 mg dichlorobis(triphenylphosphine)palladium(II) and the flask flushed (5x) with carbon monoxide. The mixture was then heated to 90° C. on an oil bath under a carbon monoxide atmosphere. After 16 hours, the mixture was cooled to room temperature, diluted with ethyl acetate and washed with water and brine. The organic portion was dried over sodium sulfate and concentrated in vacuo. Purification by flash chromatography on silica gel (ethyl acetate:hexane, 35:65; then chloroform:methanol, 95:5) gave the title compound (14 mg).

Step 6.2B 7-chloro-3-(3,5-dimethylphenyl)-4-(2-piperidin-2-yl-ethoxy)-6-(pyridine-2-carbonyl)-1H-quinolin-2-one The title compound was prepared essentially as described in EXAMPLE 5, Step B from 14 mg of 2-{2-[7-chloro-3-(3,5-dimethylphenyl)-2-oxo-6-(pyridine-2-carbonyl)-1,2-dihydroquinolin-4-yloxy]-ethyl}-piperidine-1-carboxylic acid tert-butyl ester to give 12 mg of product. MASS: 516 (M+H)

EXAMPLE 6.3

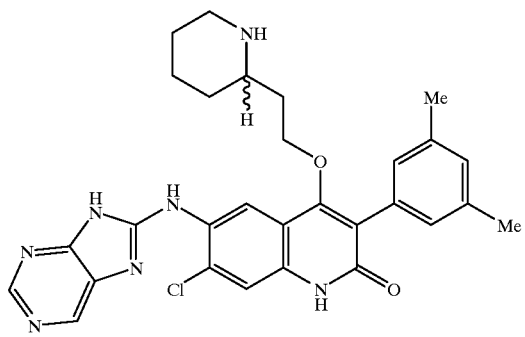

7-chloro-3-(3,5-dimethylphenyl)-4-(2-piperidin-2-yl-ethoxy)-6-(9H-purin-8-ylamino)-1H-quinolin-2-one Step 6.3A 2-{2-[7-chloro-3-(3,5-dimethylphenyl)-2-oxo-6-(9H-purin-8-ylamino)-1,2-dihydroquinolin-4-yloxy]-ethyl}-piperidine-1-carboxylic acid tert-butyl ester To a solution of 2-{2-[7-chloro-3-(3,5-dimethylphenyl)-6-isothiocyanato-2-oxo-1,2-dihydroquinolin-4-yloxy]-ethyl}-piperidine-1-carboxylic acid tert-butyl ester (210 mg in 5 mL toluene) was added 250 mg mercury(II) oxide followed by 130 mg 4,5-diaminopyrimidine and the mixture heated to reflux on an oil bath. After 48 hours, the mixture was cooled to room temperature and the reaction quenched by the addition of 2N hydrochloric acid (4 mL). The solvents were removed in vacuo and the residue treated with 2N ammonia in methanol (10 mL) then concentrated once again. The residue was washed with chloroform and the solids removed by filtration. Concentration of the organics and purification by flash chromatography on silica gel (ethyl acetate:hexane, 1:1; then chloroform:2N ammonia in methanol, 9:1) gave the title compound (10 mg).

Step 6.3B 7-chloro-3-(3,5-dimethylphenyl)-4-(2-piperidin-2-yl-ethoxy)-6-(9H-purin-8-ylamino)-1H-quinolin-2-one The title compound was prepared essentially as described in EXAMPLE 5, Step B from 10 mg of 2-{2-[7-chloro-3-(3,5-dimethylphenyl)-2-oxo-6-(9H-purin-8-ylamino)-1,2-dihydroquinolin-4-yloxy]-ethyl}-piperidine-1-carboxylic acid tert-butyl ester to give the final product (6 mg). MASS: 544 (M+H)

EXAMPLE 6.4

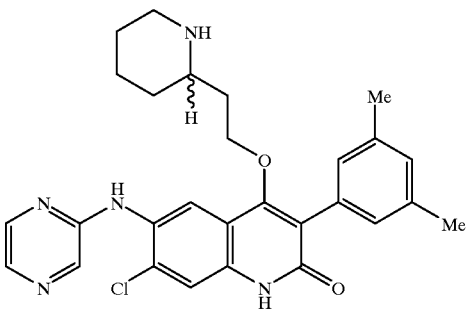

7-chloro-3-(3,5-dimethylphenyl)-4-(2-piperidin-2-yl-ethoxy)-6-(pyrazin-2-ylamino)-1H-quinolin-2-one Step 6.4A 2-{2-[7-chloro-3-(3,5-dimethylphenyl)-2-oxo-6-(pyrazin-2-ylamino)-1,2-dihydro-quinolin-4-yloxy]-ethyl}-piperidine-1-carboxylic acid tert-butyl ester To a suspension of 2-{2-[6-amino-7-chloro-3-(3,5-dimethylphenyl)-2-oxo-1,2-dihydro-quinolin-4-yloxy]-ethyl}-piperidine-1-carboxylic acid tert-butyl ester (prepared essentially as described in Example 1, 100 mg in 1 mL chloropyrazine) was added 500 mg zinc bromide and the mixture heated to 150° C. on an oil bath. After 3 hours, the mixture was cooled to room temperature, diluted with ethyl acetate and filtered through diatomaceous earth. The volatile organics were removed in vacuo and the residue dissolved in ethyl acetate, washed with water and the organic portion dried over sodium sulfate. Purification of the concentrate by flash chromatography on silica gel (ethyl acetate:hexane, 1:1) to give the title compound (12 mg).

Step 6.4B 7-chloro-3 -(3,5 -dimethylphenyl)-4-(2-piperidin-2-yl-ethoxy)-6-(pyrazin-2-ylamino)-1H-quinolin-2-one The title compound was prepared essentially as described in EXAMPLE 5, Step B from 12 mg of 2-{2-[7-chloro-3-(3,5-dimethylphenyl)-2-oxo-6-(pyrazin-2-ylamino)-1,2-dihydro-quinolin-4-yloxy]-ethyl}-piperidine-1-carboxylic acid tert-butyl ester to give the final product (8 mg). MASS: 504 (M+H)

EXAMPLE 6.5

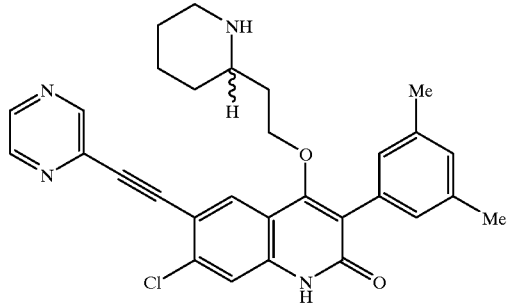

7-chloro-3-(3,5-dimethylphenyl)-4-(2-piperidin-2-yl-ethoxy)-6-pyrazin-2-ylethynyl-1H-quinolin-2-one Step 6.5A 2-{2-[7-chloro-3-(3,5-dimethylphenyl)-6-ethynyl-2-oxo-1,2-dihydroquinolin-4-yloxy]-ethyl}-piperidine-1-carboxylic acid tert-butyl ester To a suspension of 2-{2-[7-chloro-3-(3,5-dimethylphenyl)-6-iodo-2-oxo- 1,2-dihydroquinolin-4-yloxy]-ethyl}-piperidine-1-carboxylic acid tert-butyl ester (EXAMPLE 4.2 Step B, 200 mg in 3 mL N,N-dimethylformamide) was added tetrakis(triphenylphosphine)palladium (18 mg) followed by copper (I) iodide (30 mg), n-propylamine (0.26 mL) and trimethylsilylacetylene (0.45 mL) and the mixture sealed in a thick-walled tube. This was heated to 95° C. on an oil bath for 10 hours, then cooled to room temperature and diluted with diethyl ether. This was washed successively with water and brine and the combined organics dried over magnesium sulfate. Purification of the concentrate by flash chromatography on silica gel (ethyl acetate:hexane, 30:70; then 40:60) gave a mixture of the title compound and the corresponding trimethylsilyl derivative (155 mg). This material was converted to the title compound by treatment with 4.4 mg of potassium carbonate in 2 mL methanol. After 1 hour, the mixture was diluted with methylene chloride, washed with half-saturated sodium chloride, then brine and dried over magnesium sulfate. Purification of the concentrate by flash chromatography on silica gel (ethyl acetate:hexane, 30:70; then 40:60) gave the title compound (127 mg).

Step 6.5B 2-{2-[7-chloro-3-(3,5-dimethylphenyl)-2-oxo-6-pyrazin-2-ylethynyl-1,2-dihydroquinolin4-yloxy]-ethyl}-piperidine-1-carboxylic acid tert-butyl ester To a solution of 2-{2-[7-chloro-3-(3,5-dimethylphenyl)-6-ethynyl-2-oxo-1,2-dihydroquinolin-4-yloxy]-ethyl}-piperidine-1-carboxylic acid tert-butyl ester (123 mg in 1.5 mL N,N-dimethylformamide) was added tetrakis(triphenylphosphine)palladium (13 mg) followed by copper (I) iodide (22 mg), n-propylamine (0.19 mL) and chloropyrazine (0.026 mL) and the mixture heated to 90° C. on an oil bath. After 10 minutes, the mixture was cooled to room temperature, diluted with diethyl ether and washed successively with water and brine then dried over magnesium sulfate. Purification of the concentrate by flash chromatography on silica gel (ethyl acetate:hexane, 30:70; then 40:60; then 50:50) gave the title compound (69 mg).

Step 6.5C 7-chloro-3-(3,5-dimethylphenyl)-4-(2-piperidin-2-yl-ethoxy)-6-pyrazin-2-ylethynyl-1H-quinolin-2-one The title compound was prepared essentially as described in EXAMPLE 5, Step B from 22 mg of 2-{2-[7-chloro-3-(3,5-dimethylphenyl)-2-oxo-6-pyrazin-2-ylethynyl-1,2-dihydroquinolin-4-yloxy]-ethyl}-piperidine-1-carboxylic acid tert-butyl ester to give the final product (18 mg). MASS 513 (M+H)

EXAMPLE 6.6

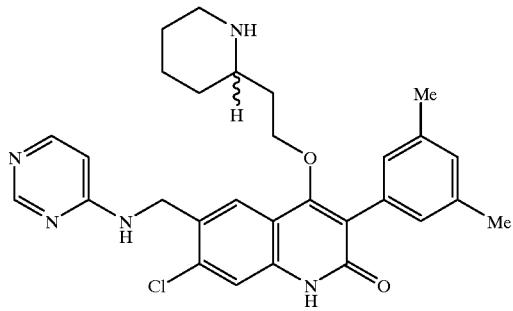

7-chloro-3-(3,5-dimethylphenyl)-4-(2-piperidin-2-yl-ethoxy)-6-(pyrimidin-4-ylaminomethyl)-1H-quinolin-2-one Step 6.6A 2-{2-[7-chloro-3-(3,5-dimethylphenyl)-6-(methoxy-methylcarbamoyl)-2-oxo-1,2-dihydroquinolin-4-yloxy]-ethyl}-piperidine-1-carboxylic acid tert-butyl ester To a solution of N,O-dimethylhydroxylamine (1.14 g in 50 mL dry methylene chloride) was added 1.5 mL triethylamine followed by 4-[2-(1-tert-butoxycarbonylpiperidin-2-yl)-ethoxy]-7-chloro-3-(3,5-dimethylphenyl)-2-oxo-1,2-dihydroquinoline-6-carboxylic acid (EXAMPLE 4.1, Step F, 1.35 g), 1-(3-dimethylaminopropyl)-3-ethylcarbodiimide hydrochloride (EDC, 1.35 g) and 4-dimethylaminopyridine (400 mg) and the mixture stirred at room temperature. After 36 hours, the mixture was concentrated in vacuo and the residue purified by flash chromatography on silica gel (ethyl acetate) to give the title compound (1.18 g).

Step 6.6B 2-{2-[7-chloro-3-(3,5-dimethylphenyl)-6-formyl-2-oxo-1,2-dihydroquinolin-4-yloxy]-ethyl}-piperidine-1-carboxylic acid tert-butyl ester To a solution of 2-{2-[7-chloro-3-(3,5-dimethylphenyl)-6-(methoxy-methylcarbamoyl)-2-oxo-1,2-dihydroquinolin-4-yloxy]-ethyl}-piperidine-1-carboxylic acid tert-butyl ester (1.18 g in dry tetrahydrofuran) was added 3.9 mL of a 1M solution of lithium aluminum hydride and the mixture stirred at room temperature. After 2 hours, the reaction was quenched by the addition of saturated ammonium chloride solution. The mixture was filtered through diatomaceous earth and the filtrate extracted with ethyl acetate. The organics were then dried over magnesium sulfate and concentrated in vacuo to give the crude title compound (900 mg).

Step 6.6C 2-{2-[7-chloro-3-(3 5-dimethylphenyl)-2-oxo-6-(pyrimidin-4-yliminomethyl)-1,2-dihydroquinolin-4-yloxy]-ethyl}-piperidine-1-carboxylic acid tert-butyl To a solution of 2-{2-[7-chloro-3-(3,5-dimethylphenyl)-6-formyl-2-oxo-1,2-dihydroquinolin-4-yloxy]-ethyl}-piperidine-1-carboxylic acid tert-butyl ester (360 mg in 150 mL toluene) was added benzotriazole (79 mg) followed by 4-aminopyrimidine (129 mg) and a catalytic amount of p-toluenesulfonic acid. The flask was fitted with a Dean-Stark trap and the mixture heated to reflux on an oil bath. After 20 hours, the mixture was cooled to room temperature and the volatile organics removed in vacuo. The residue was dissolved in chloroform then washed with 2N sodium hydroxide. The organic portion was dried over magnesium sulfate, concentrated in vacuo and purified by flash chromatography on silica gel (ethyl acetate:hexane, 3:2) to give the title compound (300 mg).

Step 6.6D 2-{2-[7-chloro-3-(3,5-dimethylphenyl)-2-oxo-6-(pyrimidin-4-ylaminomethyl)-1,2-dihydroquinolin-4-yloxy]-ethyl}-piperidine-1-carboxylic acid tert-butyl ester To a solution of 2-{2-[7-chloro-3-(3,5-dimethylphenyl)-2-oxo-6-(pyrimidin-4-yliminomethyl)-1,2-dihydroquinolin-4-yloxy]-ethyl )-piperidine-1-carboxylic acid tert-butyl ester (36 mg in 2 mL dry tetrahydrofuran) at −10° C. was added a 1M solution of lithium aluminum hydride (2 mL) and the mixture stirred at low temperature. After 2 hours, the reaction was quenched by the addition of water, filtered and the organic portion concentrated in vacuo. Purification by preparative tlc on silica gel gave the title compound.(12 mg).

Step 6.6E 7-chloro-3-(3,5-dimethylphenyl)-4-(2-piperidin-2-yl-ethoxy)-6-(pyrimidin-4-ylaminomethyl)-1H-quinolin-2-one The title compound was prepared essentially as described in EXAMPLE 5, Step B from 12 mg of 2-{2-[7-chloro-3-(3,5-dimethylphenyl)-2-oxo-6-(pyrimidin-4-ylaminomethyl)-1,2-dihydroquinolin-4-yloxy]-ethyl}-piperidine-1-carboxylic acid tert-butyl ester to give the final product (6 mg). MASS: 518 (M+H)

Following a procedure similar to that described above, the following compounds were prepared:

-continued
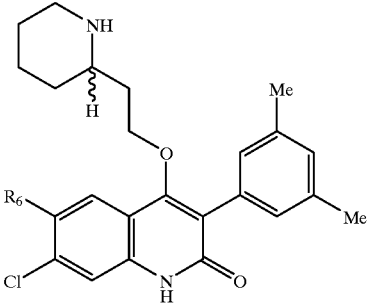
| Ex. # | R$_6$ | m/e |
|---|---|---|
| 6A | 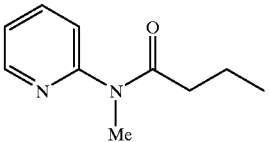 | 573 (M + H) |
| 6B | 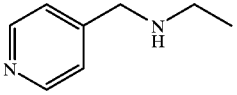 | 531 (M + H) |
| 6C | 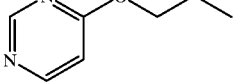 | 533 (M + H) |
| 6D | 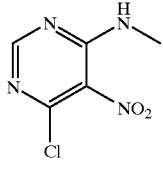 | |
| 6E | 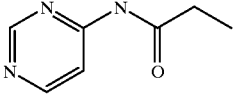 | 546 (M + H) |
| 6F | 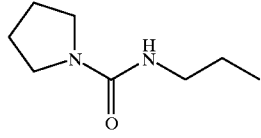 | 551 (M + H) |
| 6G | 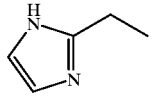 | 491 (M + H) |
| 6H | 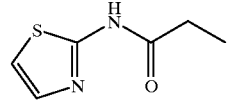 | 551 (M + H) |
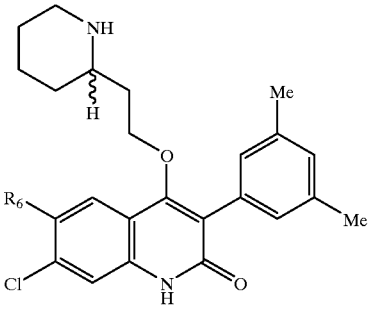
| Ex. # | R$_6$ | m/e |
|---|---|---|
| 6I | 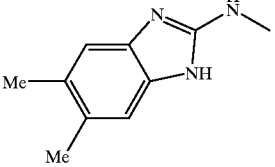 | 570 (M + H) |
| 6J | 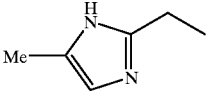 | 505 (M + H) |
| 6K | 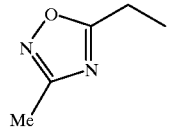 | 507 (M + H) |
| 6L | 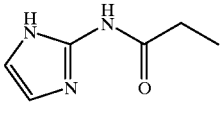 | 535 (M + H) |
| 6M | 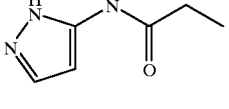 | 535 (M + H) |
| 6N | 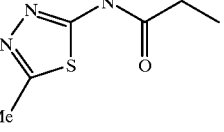 | 566 (M + H) |
| 6O | 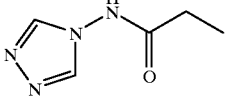 | 535 (M + H) |
| 6P | 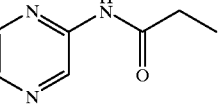 | 546 (M + H) |

-continued

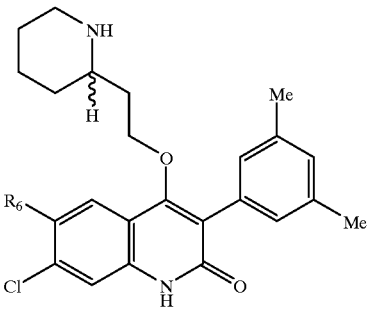

| Ex. # | R6 | m/e |
|---|---|---|
| 6Q | pyrimidin-2-yl-NH-C(O)-CH2CH3 | 546 (M + H) |
| 6R | EtO-C(O)-thiazole-NHMe | 581 (M + H) |
| 6S | pyrimidin-4-yl-NH-C(O)-CH(Me)- | 560 (M + H) |
| 6T | pyridin-2-yl-C(O)- | — |
| 6U | pyridin-2-yl-C≡C- | 512 (M + H) |

EXAMPLE 7.1

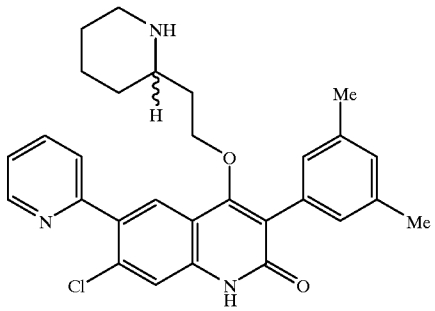

7-chloro-3-(3,5-dimethylphenyl)-4-(2-piperidin-2-yl-ethoxy)-6-pyridin-2-yl-1H-quinolin-2-one Step 7.1A 2-{2-[7-chloro-3-(3,5-dimethylphenyl)-2-oxo-6-pyridin-2-yl-1,2-dihydroquinolin-4-yloxy]-ethyl}-1-piperidine-1-carboxylic acid tert-butyl ester To a solution of 2-{2-[7-chloro-3-(3,5-dimethylphenyl)-6-iodo-2-oxo-1,2-dihydro-quinolin-4-yloxy]-ethyl}-piperidine-1-carboxylic acid tert-butyl ester (EXAMPLE 4.2 Step B, 150 mg in 3 mL dry toluene) was added 104 mg of 2-tributylstannanylpyridine followed by 50 mg lithium chloride. To this, 8 mg of dichlorobis(triphenylphosphine) palladium (II) was added and the mixture heated to reflux on an oil bath. After 24 hours, the mixture was cooled to room temperature and diluted with 5 mL ethyl acetate/5 mL water. The aqueous layer was saturated with potassium fluoride and stirred vigorously for 15 minutes. The organic layer was isolated and washed with water and brine then dried over magnesium sulfate. Purification of the concentrate by flash chromatography on silica gel (ethyl acetate:hexane, 3:2) gave the title compound (140 mg).

Step 7.1B 7-chloro-3-(3,5-dimethylphenyl)-4-(2-piperidin-2-yl-ethoxy)-6-pyridin-2-yl-1H-quinolin-2- one To a solution of 2-(2-[7-chloro-3-(3,5-dimethylphenyl)-2-oxo-6-pyridin-2-yl-1,2-dihydroquinolin-4-yloxy]-ethyl}-piperidine-1-carboxylic acid tert-butyl ester in 2.0 dry methylene chloride was added a few drops of anisole followed by 2.0 mL of trifluoroacetic acid and the mixture stirred at room temperature. After 1.5 hours, the solvents were removed in vacuo and the resulting residue purified by reverse-phase mplc (C-8, methanol:0.1% aqueous trifluoroacetic acid, 55:45) to give the title compound (112 mg). MASS: 488 (M+H)

EXAMPLE 7.2

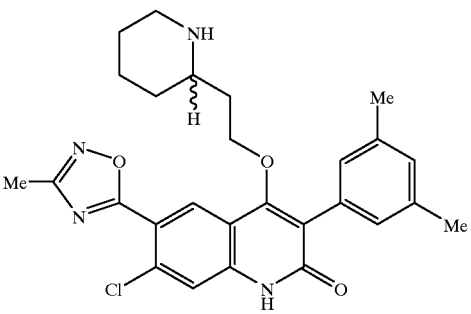

7-chloro-3-(3,5-dimethylphenyl)-6-(3-methyl-[1,2,4]oxadiazol-5-yl)-4-(2piperidin-2-yl-ethoxy)-1H-quinolin-2-one Step 7.2A 2-{2-[7-chloro-3-(3,5-dimethylphenyl)-6-(3-methyl-[1,2,4]oxadiazol-5-yl)-2-oxo-1,2-dihydroquinolin-4-yloxy]-ethyl}-piperidine-1-carboxylic acid tert-butyl ester To a solution of 2-{2-[7-chloro-3-(3,5-dimethylphenyl)-6-iodo-2-oxo-1,2-dihydro-quinolin-4-yloxy]-ethyl}-piperidine-1-carboxylic acid tert-butyl ester (EXAMPLE 4.2 Step B, 200 mg in a mixture of 3 mL dry N,N-dimethylformamide and 0.9 mL triethylamine) was added 118 mg of acetamide oxime followed by 11 mg of dichlorobis(triphenylphosphine) palladium (II) and the mixture heated to reflux on an oil bath under an atmosphere of carbon monoxide. After 12 hours, the mixture was cooled to room temperature and diluted with ethyl acetate and 0.5N hydrochloric acid. This was extracted with ethyl acetate and the organic portion washed with brine then dried over sodium sulfate. Purification of the concentrate by flash chromatography on silica gel (ethyl acetate:hexane, 1:4; then 3:7) gave the title compound (88 mg).

Step 7.2B 7-chloro-3-(3,5-dimethylphenyl-6-(3-methyl-[1 2,4]oxadiazol-5-yl)-4-(2-piperidin-2-yl-ethoxy)-1H-quinolin-2-one The title compound was prepared essentially as described in EXAMPLE 5, Step B from 81 mg of 2-{2-[7-chloro-3-(3,5-dimethylphenyl)-6-(3 -methyl-[1,2,4]oxadiazol-5 -yl)-2-oxo-1,2-dihydroquinolin-4-yloxy]-ethyl}-piperidine-1-carboxylic acid tert-butyl ester to give the final product (63 mg).

| Ex. # | R₆ | m/e |
|---|---|---|
| 7A | (2-methylfuran) | 477 (M + H) |
| 7B | (3-methylpyridine) | 488 (M + H) |
| 7C | (3-methylfuran) | 475 (M + H) |
| 7D | (4-methylpyridine) | 488 (M + H) |
| 7E | (methylpyrazine) | 489 (M + H) |
| 7F | (pyrazinyl-methyloxadiazole) | 557 (M + H) |

Following a procedure similar to that described above, the following compounds were prepared:

| Ex. # | R₆ | m/e |
|---|---|---|
| 7A | (2-methylfuran) | 477 (M + H) |
| 7B | (3-methylpyridine) | 488 (M + H) |
| 7C | (3-methylfuran) | 475 (M + H) |
| 7D | (4-methylpyridine) | 488 (M + H) |
| 7E | (methylpyrazine) | 489 (M + H) |
| 7F | (pyrazinyl-methyloxadiazole) | 557 (M + H) |

EXAMPLE 8

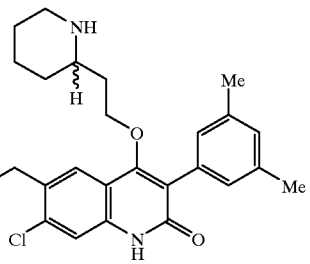

7-chloro-3 -(3,5-dimethylphenyl)-4-(2-piperidin-2-yl-ethoxy)-6-(3-p-tolyl-[1,2,4]oxadiazol-5-ylmethyl)-1H-quinolin-2-one Step 8A 2-{2-[7-chloro-6-(2,3-dihydroxypropyl)-3-(3,5-dimethylphenyl)-2-oxo-1,2-dihydroquinolin-4-yloxy]-ethyl}-piperidine-1-carboxylic acid tert-butyl ester To a solution of 2-{2-[6-allyl-7-chloro-3-(3,5-dimethylphenyl)-2-oxo-1,2-dihydroquinolin-4-yloxy]-ethyl}-piperidine-1-carboxylic acid tert-butyl ester (EXAMPLE 4.1 Step E, 6.0 g in a mixture of 80 mL tert-butanol, 24 mL tetrahydrofuran and 8 mL water) was added 1.4 g 4-methylmorpholine N-oxide followed by 140 mg osmium tetraoxide and the mixture stirred at room temperature. After 20 hours, the mixture was concentrated in vacuo and the residue dissolved in ethyl acetate and washed sequentially with water and brine. The combined organics were dried over sodium sulfate and purified by flash chromatography on silica gel (ethyl acetate:hexane, 1:1; then methylene chloride:10% ammonium hydroxide in methanol, 9:1) to give the title compound (5.7 g).

Step 8B 2-{2-[6-carboxymethyl-7-chloro-3-(3,5-dimethylphenyl)-2-oxo-1,2-dihydroquinolin-4-yloxy]-ethyl}-piperidine-1-carboxylic acid tert-butyl ester To a solution of -{2-[7-chloro-6-(2,3-dihydroxypropyl)-3-(3,5-dimethylphenyl)-2-oxo-1,2-dihydroquinolin-4-yloxy]-ethyl}-piperidine-1-carboxylic acid tert-butyl ester (4.3 g in a mixture of 200 mL methanol and 3 mL pyridine) at 0° C. was added 7.4 g lead(IV) acetate in portions over 5 minutes and the mixture stirred at low temperature. After 10 minutes, the reaction was quenched by the addition of sodium sulfite and the mixture extracted with methylene chloride. The organic portion was washed with brine, dried over sodium sulfite and concentrated in vacuo to give the crude aldehyde intermediate.

The aldehyde was solvated in 200 mL tert-butanol and then 24 mL of a 1.25M solution of sodium dihydrogenphosphate was added followed by the dropwise addition of 44.5 mL of a 1M aqueous solution of potassium permanganate. After 2 hours, the reaction was quenched by the addition of saturated aqueous sodium sulfite. The pH of the solution was adjusted to 3 by the addition of IN hydrochloric acid then the mixture was extracted with ethyl acetate, washed with brine and dried over sodium sulfate. Purification of the concentrate by flash chromatography on silica gel (ethyl acetate-:hexane 3:7=1% acetic acid) gave the title compound (2.8 g).

Step 8C 2-{2-[7-chloro-3-(3,5-dimethylphenyl)-2-oxo-6-(3-p-tolyl-[1,2,4]oxadiazol-5-ylmethyl)-1,2-dihydroquinolin-4-yloxy]-ethyl}-piperidine-1-carboxylic acid tert-butyl ester To a solution of 2-{2-[6-carboxymethyl-7-chloro-3-(3,5-dimethylphenyl)-2-oxo-1,2-dihydroquinolin-4-yloxy]-ethyl}-piperidine-1-carboxylic acid tert-butyl ester (57 mg in 0.60 mL dry methylene chloride) was added 20 mg N-hydroxy-4-methylbenzamidine followed by 30 mg 1-(3-dimethylaminopropyl)-3-ethylcarbodiimide hydrochloride (EDC) and 6 mg dimethylaminopyridine and the mixture stirred at room temperature. After 6 hours, the mixture was diluted with methylene chloride, washed with water and the organic portion concentrated in vacuo. Purification of the concentrate by flash chromatography on silica gel (methylene chloride:methanol, 98:2; then 97:3) gave the intermediate ester derivative (61 mg). The ester was dissolved in 2.5 mL toluene and heated to reflux on an oil bath. After 2.5 hours, the mixture was cooled to room temperature and the concentrate purified by flash chromatography on silica gel (ethyl acetate:hexane, 1:4; then 2:3) to give the title compound (51 mg).

Step 8D 7-chloro-3-(3,5-dimethylphenyl)-4-(2-piperidin-2-yl-ethoxy)-6-(3-p-tolyl-[1,2,4]oxadiazol-5-ylmethyl)-1H-quinolin-2-one The title compound was prepared essentially as described in EXAMPLE 5, Step B from 51 mg of 2-{2-[7-chloro-3-(3,5-dimethylphenyl)-2-oxo-6-(3-p-tolyl-[1,2,4]oxadiazol-5-ylmethyl)-1,2-dihydroquinolin-4-yloxy]-ethyl}-piperidine-1-carboxylic acid tert-butyl ester to give the final product (31 mg). MASS 583 (M+H)

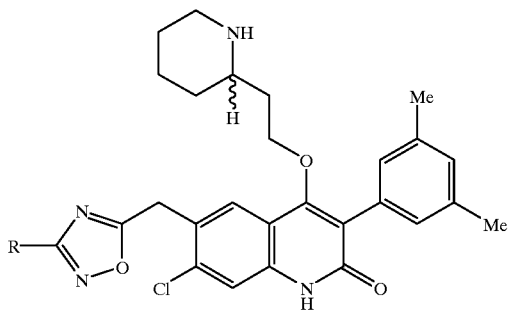

Following a procedure similar to that described above, the following compounds were prepared:

| Ex. # | R | m/e |
|---|---|---|
| 8A | MeO-C6H4- | 600 (M + H) |
| 8B | 4-pyridyl | 570 (M + H) |
| 8C | pyrazinyl | 571 (M + H) |
| 8D | phenyl | 569 (M + H) |
| 8E | 2-pyridyl | 571 (M + H) |
| 8F | 3-pyridyl | 571 (M + H) |
| 8G | MeOOC-C6H4- | 629 (M + H) |
| 8H | 3-methylphenyl | 583 (M + H) |

EXAMPLE 9

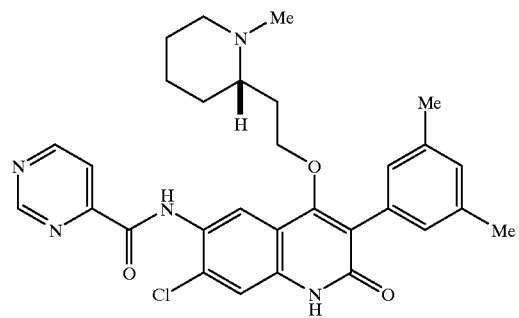

(S)-pyrimidine-4-carboxylic acid {7-chloro-3-(3,5-dimethylphenyl)-4-[2-(1-methylpiperidin-2-yl)-ethoxy]-2-oxo-1,2-dihydroquinolin-6-yl}-amide To a solution of pyrimidine-4-carboxylic acid (S)-[7-chloro-3-(3,5-dimethylphenyl)-2-oxo-4-(2-piperidin-2-yl-ethoxy)-1,2-dihydroquinolin-6-yl]-amide (prepared essentially as described in EXAMPLE 2, 9 mg in 0.40 mL methanol) was added 6 mg paraformaldehyde followed by 20 mg powdered 4A molecular sieves and 0.01 mL acetic acid and the mixture stirred at room temperature for 10 minutes. At this time, 5 mg sodium cyanoborohydride was added and the stirring continued. After 2 hours, 0.5 mL tetrahydrofuran was added to ensure homogeneity and after 60 hours the reaction was quenched by the addition of water. The reaction mixture was extracted with methylene chloride and the combined organics washed with brine and dried over sodium sulfate. Purification of the concentrate by flash chromatography on silica gel (methylene chloride:10% ammonium hydroxide in methanol, 95:5; then 92:8) gave the title compound (6.7 mg). MASS: 546 (M+H)

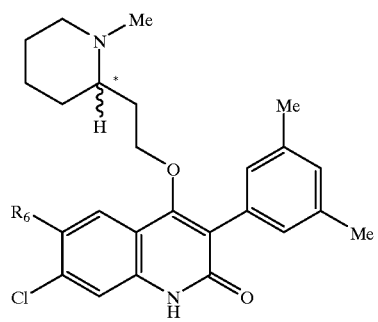

Following a procedure similar to that described above, the following compounds were prepared:

| Ex. # | R₆ | m/e |
|---|---|---|
| 9A |  | 546 (M + H) |
| 9B |  | 546 (M + H) *S-enantiomer |
| 9C |  | 560 (M + H) *S-enantiomer |
| 9D |  | 586 (M + H) *S-enantiomer |
| 9E |  | 680 (M + H) *S-enantiomer |
| 9F |  | 548 (M + H) *S-enantiomer |
| 9G |  |  |
| 9H |  |  |

EXAMPLE 10

The following compounds were prepared essentially as described in EXAMPLES 2 and 4.

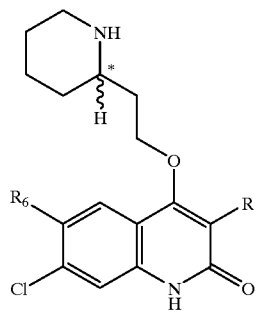
| Ex. # | R | R6 | m/e |
|---|---|---|---|
| 10A | 3,5-dichlorophenyl | pyrimidine-4-C(O)NH-Me | 572 (M + H) |
| 10B | 3,5-dichlorophenyl | pyridin-4-yl-NHC(O)Me | 571 (M + H) |
| 10C | 3,5-dichlorophenyl | pyrimidin-4-yl-NHC(O)Me | 572 (M + H) |
| 10D | 3,5-dichlorophenyl | pyrimidin-4-yl-N(Me)C(O)Me *N-Me | 586 (M + H) |
| 10E | 2,4-dimethylphenyl | pyrimidin-4-yl-NHC(O)Me | |
| 10F | 2,4-dimethylphenyl | pyrimidine-4-C(O)NH-Me | |
| 10G | 3,5-dichlorophenyl | pyrimidin-4-yl-NHC(O)Me *S-enantiomer | 572 (M + H) |

-continued

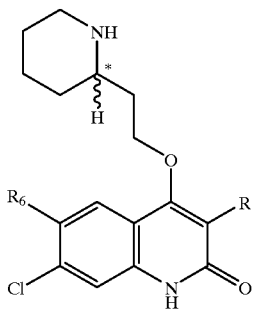

| Ex. # | R | R6 | m/e |
|---|---|---|---|
| 10H | 3,5-diCl-phenyl | pyrimidin-4-yl-NHC(O)- *S-enantiomer, N-Me | 586 (M + H) |
| 10I | 2,4-diMe-phenyl | pyrimidin-4-yl-NHC(O)- *S-enantiomer | 532 (M + H) |
| 10J | 3,4-diCl-phenyl | pyrimidin-4-yl-NHC(O)- *S-enantiomer | 572 (M + H) |
| 10J | 3,4-diCl-phenyl | pyrimidin-4-yl-NHC(O)- *S-enantiomer, N-Me | 586 (M + H) |
| 10K | 2,4-diMe-phenyl | pyrimidin-4-yl-NHC(O)- *S-enantiomer, N-Me | 546 (M + H) |
| 10L | 3,4-diCl-phenyl | 1,2,5-thiadiazol-3-yl-NHC(O)- *S-enantiomer | 538 (M + H) |
| 10M | 2,4-diMe-phenyl | 1,2,5-thiadiazol-3-yl-NHC(O)- *S-enantiomer | 644 (M + H) |

-continued

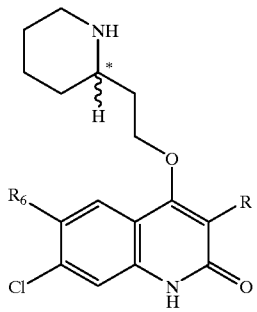

| Ex. # | R | R$_6$ | m/e |
|---|---|---|---|
| 10N | 2-Me, 4-Me, with I (2,5-dimethyl-iodophenyl) | pyrimidin-4-yl-NHAc *S-enantiomer | 576 (M + H) |
| 10O | 2-Me, 5-Me, COOMe | pyrimidin-4-yl-NHAc *S-enantiomer | 546 (M + H) |
| 10P | 2,3,5-triMe phenyl | pyrimidin-4-yl-NHAc *S-enantiomer | |
| 10Q | 2,3,5-triMe phenyl | pyrimidin-4-yl-NHAc *S-enantiomer, N-Me | 560 (M + H) |
| 10R | 2,3,5-triMe phenyl | 1,2,5-thiadiazol-3-yl-NHAc *S-enantiomer | 552 (M + H) |
| 10S | 2-Me, 5-Me, vinyl | pyrimidin-4-yl-NHAc *S-enantiomer | 544 (M + H) |
| 10T | 2-Me, 5-Me, Et | pyrimidin-4-yl-NHAc *S-enantiomer | 546 (M + H) |

-continued

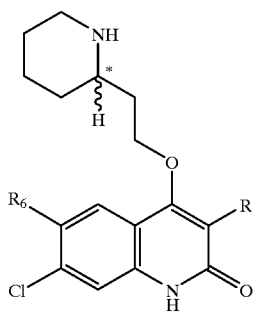

| Ex. # | R | R6 | m/e |
|---|---|---|---|
| 10U | 2-Me, 5-Me phenyl with phenylethynyl | 4-acetamidopyrimidine *S-enantiomer | 618 (M + H) |
| 10V | 2-Me, 5-Me phenyl with phenylethyl | 4-acetamidopyrimidine *S-enantiomer | 622 (M + H) |
| 10W | 2-Me, 5-Me phenyl with pentynyl (Me) | 4-acetamidopyrimidine *S-enantiomer | 598 (M + H) |
| 10X | 2-Me, 5-Me phenyl with cis-pentenyl (Me) | 4-acetamidopyrimidine *S-enantiomer | 600 (M + H) |
| 10Y | 2-Me, 5-Me phenyl with pentyl (Me) | 4-acetamidopyrimidine *S-enantiomer | 602 (M + H) |

EXAMPLE 11

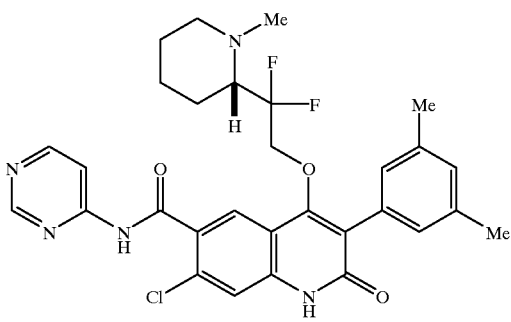

(S)-7-chloro-4-[2,2-difluoro-2-(1-methylpiperidin-2-yl)-ethoxy]-3-(3,5-dimethylphenyl)-2-oxo-1,2-dihydroquinoline-6-carboxylic acid pyrimidin-4-ylamide Step 11A 7-chloro-3-(3,5-dimethylphenyl)-4-hydroxy-2-oxo-1,2-dihydroquinoline-6-carboxylic acid pyrimidin-4-ylamide To 20 mL dry methylsulfoxide was added sequentially 7-chloro-3-(3,5-dimethylphenyl)-4-hydroxy-6-iodo-1H-quinolin-2-one (EXAMPLE 4.2 Step B, 1.0 g), 4-dimethylaminopyridine (860 mg), 4-aminopyrimidine (90 mg), [1,1'-bis(diphenylphosphino)ferrocene)-dichloropalladium (II) and the mixture heated to 100° C. under an atmosphere of carbon monoxide. After 72 hours, the mixture was cooled to room temperature and poured into 200 mL ice/water. The pH of the resulting solution was adjusted to pH4 by the addition of acetic acid. The resulting solids were collected by filtration and then re-purified by flash chromatography on silica gel (chlorofonm:methanol, 95:5) to give the title compound (400 mg).

Step 11B (S)-7-chloro-4-[2,2-difluoro-2-(1-methylpiperidin-2-yl)-ethoxy]-3-(3,5-dimethylphenyl)-2-oxo-1,2-dihydroquinoline-6-carboxylic acid pyrimidin-4-ylamide To a solution of (S)-2-(2-chloro-1,1-difluoroethyl)-1-methylpiperidine (39 mg in 1.5 mL N,N-dimethylformamide) was added 7-chloro-3-(3,5-dimethylphenyl)-4-hydroxy-2-oxo-1,2-dihydroquinoline-6-carboxylic acid pyrimidin-4-ylamide (64 mg), potassium bicarbonate (32 mg) and sodium iodide (25 mg) then heated to 80° C. on an oil bath. After 16 hours, the reaction was cooled to room temperature and concentrated in vacuo. Purification of the crude product by preparative tic on silica gel (chloroform:2M ammonium in methanol, 97:3) gave the title compound (56 mg). MASS: 582 (M+H)

PREPARATION OF SYNTHETIC INTERMEDIATES (S)-2-(2-chloro-1,1-difluoroethyl)-1-methylpiperidine Step A (S)-2-(diazoacetyl)piperidine-1-carboxylic acid tert-butyl ester To a solution of (S)-piperidine-1,2-dicarboxylic acid 1-tert-butyl ester (3.0 g in a mixture of 26 mL dry tetrahydrofuran and 26 mL dry diethyl ether) at −10° C. was added 1.91 mL of triethylamine followed by the dropwise addition of 1.78 mL isobutyl chloroformate. The reaction was stirred at −10° C. for 30 minutes then warmed to 0° C. Over the next hour, 26 mL of a solution of diazomethane in diethyl ether was added (prepared from: 8.0 g Diazald® in 70 mL diethyl ether; 4g potassium hydroxide; 20 mL 2-(2-ethoxyethoxy) ethanol; 6 mL water and 12 mL diethyl ether using a mini Diazald Kit) and the mixture allowed to stir at room temperature for an additional 2 hours. At this time the reaction was quenched by the addition of 3 mL acetic acid at 0° C. This was then diluted with 100 mL water and 100 mL diethyl ether, the layers separated and the aqueous portion extracted with (2×75 mL) diethyl ether. The combined organics were washed with water (75 mL), saturated sodium bicarbonate (2×75 mL) and brine (75 mL) then dried over magnesium sulfate. Removal of the solvent in vacuo and purification of the residue by flash chromatography on silica gel (hexane:ethyl acetate, 8:2) gave the title compound, 2.99 g.

Step B (S)-2-(methoxycarbonylmethyl)piperidine-1-carboxylic acid tert-butyl ester To a solution of (S)-2-(diazoacetyl)piperidine-1-carboxylic acid tert-butyl ester (5.90 g in 90 mL dry methanol) was added dropwise a solution of silver benzoate (265 mg in 3 mL triethylamine) and the mixture stirred at room temperature. After 2 hour, charcoal was added and the suspension filtered over diatomaceous earth. The mixture was concentrated in vacuo and the residue dissolved in ethyl acetate (400 mL), washed with water (2×100 mL) and brine (150 mL). The organic portion was dried over magnesium sulfate and the concentrate purified by flash chromatography on silica gel (hexane:ethyl acetate, 8:2) to give the title compound (5.47 g).

Step C 2-(difluoro-methoxycarbonylmethyl)piperidine-1-carboxylic acid tert-butyl ester To a solution of (S)-2-(methoxycarbonylmethyl)piperidine-1-carboxylic acid tert-butyl ester (1.0 g in 20 mL dry tetrahydrofuran) at −78° C. was added 19.4 mL of a 0.5M solution of potassium bis(trimethylsilyl)amide in toluene and the mixture stirred for 30 minutes. At this time, a solution of N-fluorobenzenesulfonimide (3.06 g in 10 mL dry tetrahydrofuran) was added and the mixture stirred at −78° C. for 45 minutes then 0C for an additional 45 minutes. The reaction was quenched by the addition of 50% saturated ammonium chloride and extracted with diethyl ether (3×100 mL). The combined organics were washed with water, brine and then dried over magnesium sulfate. Concentration in vacuo gave the crude title compound (1.8 g).

Step D 2,2-difluoro-2-(1-methylpiperidin-2-yl)ethanol

To a solution of 2-(difluoro-methoxycarbonylmethyl) piperidine-1-carboxylic acid tert-butyl ester (1.14 g in 30 mL dry diethyl ether) at 0° C. was added 580 mg lithium aluminum hydride and the mixture stirred at low temperature. After 15 minutes, the reaction was quenched by the sequential addition of 0.58 mL water, 0.58 mL 2N sodium hydroxide and 0.74 mL water. The mixture was stirred vigorously for 1 hour then filtered over diatomaceous earth. The filtrate was concentrated in vacuo and purified by flash chromatography on silica gel (hexane:ethyl acetate, 85:15) to give the title compound (450 mg).

Step E (S)-2-(2-chloro-1,1-difluoroethyl)-1-methylpiperidine

To a solution of 2,2-difluoro-2-(1-methylpiperidin-2-yl) ethanol (153 mg in 10 mL dry chloroform) was bubbled dry hydrogen chloride gas for a period of 5 minutes. To this solution, 0.303 mL of thionyl chloride and the mixture heated to reflux on an oil bath. After 5 hours, the mixture was cooled and the solvent removed in vacuo. The residue was re-solvated in 5 mL ethanol, concentrated in vacuo, re-solvated in ethanol and then treated with decolorizing carbon. The resulting suspension was filtered over diatomaceous earth and concentrated in vacuo to give the crude title compound (200 mg).

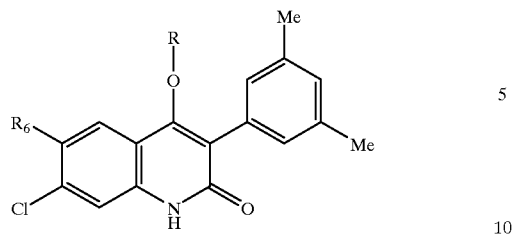
Following a procedure similar to that described above and in EXAMPLE 4, the following compounds were prepared:
| Ex. # | R | $R_6$ | m/e |
|---|---|---|---|
| 11A | | | 506 (M + H) |
| 11B | racemic | | |
| 11C | | | 518 (M + H) |
| 11D | | | 532 (M + H) |
| 11E | | | 550 (M + H) |

-continued
| Ex. # | R | R6 | m/e |
|---|---|---|---|
| 11F | 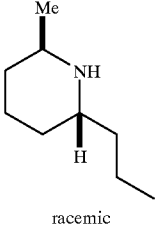 racemic | 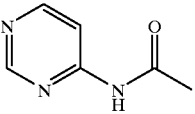 | 546 (M + H) |
| 11G | 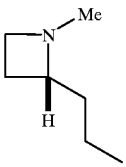 | 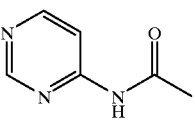 | 520 (M + H) |
| 11H | 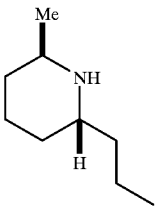 | 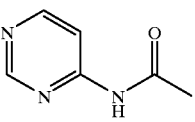 | 546 (M + H) |
| 11I | 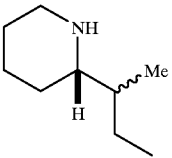 | 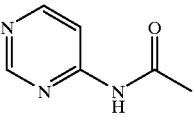 | 546 (M + H) |
| 11J | 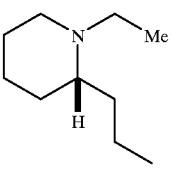 | 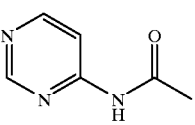 | 546 (M + H) |
| 11K | 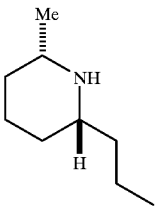 | 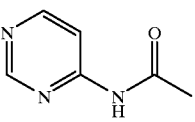 | 546 (M + H) |
| 11L | 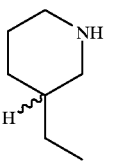 | 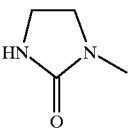 | 481 (M + H) |

-continued
| Ex. # | R | R6 | m/e |
|---|---|---|---|
| 11M | 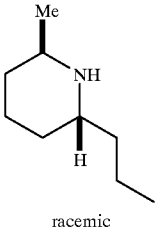 racemic | 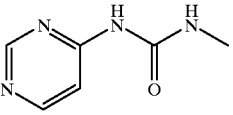 | 561 (M + H) |
| 11N | 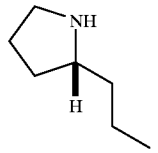 | 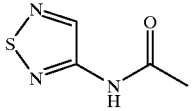 | 524 (M + H) |
| 11O | 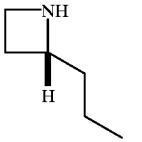 | 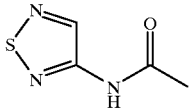 | 510 (M + H) |
| 11P | 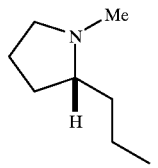 | 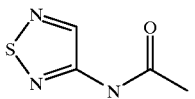 | 538 (M + H) |
| 11Q | 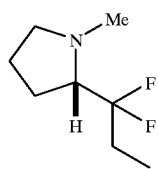 | 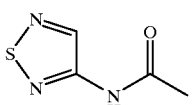 | 568 (M + H) |
| 11R | 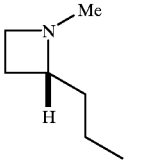 | 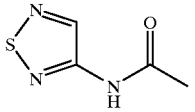 | 524 (M + H) |

EXAMPLE 12
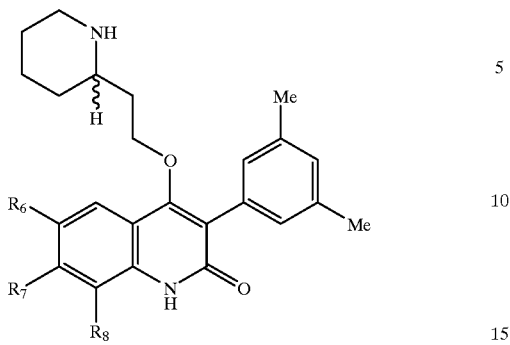
Following a procedure similar to that described in EXAMPLES 2 and 4, the following compounds were prepared:
| Ex. # | R$_6$ | R$_7$ | R$_8$ | m/e |
|---|---|---|---|---|
| 12A | H | pyrimidin-4-yl-NHC(O)NHMe | H | 513 (M + H) |
| 12B | H | pyrazin-2-yl-NHC(O)NHMe | H | 513 (M + H) |
| 12C | H | pyrazin-2-yl-C(O)NHMe | H | 497 (M + H) |
| 12D | H | pyrazin-2-yl-NHC(O)NHMe | Cl | 547 (M + H) |
| 12E | H | pyrazin-2-yl-C(O)NHMe | Cl | 547 (M + H) |
| 12F | H | pyrimidin-4-yl-NHC(O)NHMe | H | 545 (M + H) |
| 12F | H | 6-chloropyrazin-2-yl-CH$_2$C(O)NHMe | Cl | 580 (M + H) |

-continued

| Ex. # | R6 | R7 | R8 | m/e |
|---|---|---|---|---|
| 12G | pyrimidin-4-yl-NH-C(=O)- (*S-enantiomer) | $CF_3$ | H | 566 (M + H) |
| 12H | pyrimidin-4-yl-N(Me)-C(=O)- (S-enantiomer, N—Me) | $CF_3$ | H | 580 (M + H) |
| 12I | pyrazin-2-yl-N=C(NHMe)(SMe) | Cl | H | 577 (M + H) |
| 12J | pyrazin-2-yl-NH-C(=S)-NHMe | Cl | H | 563 (M + H) |
| 12K | pyrazin-2-yl-N=C(NHMe)(NH-cyclopropyl) | Cl | H | 586 (M + H) |

EXAMPLE 13

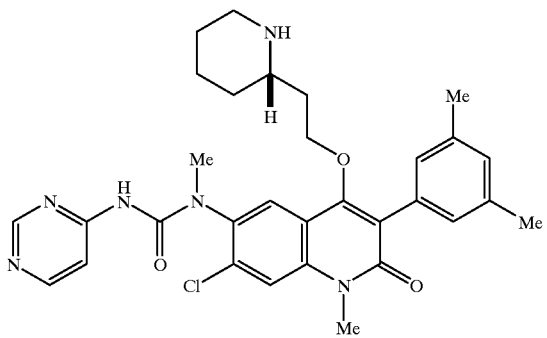

(S)-1-[7-chloro-3-(3,5-dimethylphenyl)-1-methyl-2-oxo-4-(2-piperidin-2-yl-ethoxy)-1,2-dihydroquinolin-6-yl]-1-methyl-3-pyrimidin-4-yl-urea Step 13A (S)-2-{2-[7-chloro-3-(3,5-dimethylphenyl)-1-methyl-6-(1-methyl-3-pyrimidin-4-yl-ureido)-2-oxo-1,2-dihydroquinolin-4-yloxy]-ethyl}-piperidine-1-carboxylic acid tert-butyl ester To a solution of lithium bis(trimethylamide) (0.43 mL of a 1M solution in 1.0 mL dry tetrahydrofuran) at −78° C. was added 0.198 mL hexamethylphosphoramide (HMPA) followed by a solution of (S)-2-{2-[7-chloro-3-(3,5-dimethylphenyl)-2-oxo-6-(3-pyrimidin-4-yl-ureido)-1,2-dihydroquinolin-4-yloxy]-ethyl}-piperidine-1-carboxylic acid tert-butyl ester (prepared essentially as described in EXAMPLE 1, 69 mg in 1.5 mL dry tetrahydrofuran) and the mixture stirred at low temperature for 75 minutes. At this time, 0.036 mL of iodomethane was added and the mixture warmed to 0° C. After 4 hours, the reaction was quenched by the addition of IN hydrochloric acid, extracted with methylene chloride washed with brine and dried over magnesium sulfate. Purification of the concentrate by flash chromatography on silica gel (ethyl acetate:hexane 3:7; then 5:5; then 7:3) gave the title compound (30 mg).

Step 13B (S)-1-[7-chloro-3-(3,5-dimethylphenyl)-1-methyl-2-oxo-4-(2-piperidin-2-yl-ethoxy)-1,2-dihydroquinolin-6-yl]-1-methyl-3-pyrimidin-4-yl-urea The title compound was prepared essentially as described in EXAMPLE 5, Step B from 30 mg of (S)-2-(2-[7-chloro-3-(3,5-dimethylphenyl)-1-methyl-6-(1-methyl-3-pyrimidin-4-yl-ureido)-2-oxo-1,2-dihydroquinolin-4-yloxy]-ethyl)-piperidine-1-carboxylic acid tert-butyl ester to give the final product (13 mg). MASS: 561 (M+H)

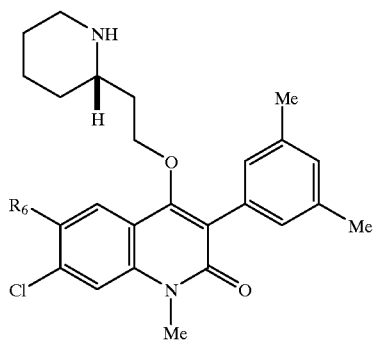

Following a procedure similar to that described above, the following compounds were prepared:

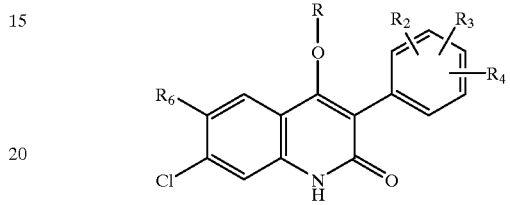

| Ex. # | R₆ | m/e |
|---|---|---|
| 13A | (pyrimidinyl)N(Me)C(O)N(Me)– | 589 (M + H) |

EXAMPLE 14

Following a procedure similar to that described in EXAMPLES 2, 4 and 11 the following compounds were prepared:

| Ex. # | R | R₆ | aryl | m/e |
|---|---|---|---|---|
| 14A | 2-piperidinyl-CH₂CH₂– | pyrimidin-4-yl-NHC(O)– | 5-methylindan-yl | 544 (M + H) |
| 14B | 2-azetidinyl-CH₂CH₂– | pyrimidin-4-yl-NHC(O)– | 2,3,5-trimethylphenyl | 518 (M + H) |
| 14C | 3-azetidinyl-CH₂CH₂– | 1,2,5-thiadiazol-3-yl-NHC(O)– | 2,3,5-trimethylphenyl | 524 (M + H) |
| 14D | N-Me-2-azetidinyl-CH₂CH₂– | pyrimidin-4-yl-NHC(O)– | 2,3,5-trimethylphenyl | 532 (M + H) |

What is claimed is:

1. The compound of the structural formula

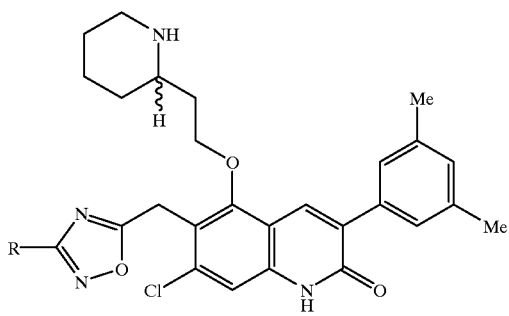

wherein R is as indicated in the table below:

| Ex. # | R |
|---|---|
| 8A | Me–C₆H₄– (p-tolyl) |
| 8B | MeO–C₆H₄– (p-methoxyphenyl) |
| 8C | 4-pyridyl |
| 8D | pyrazinyl |
| 8E | phenyl |
| 8F | 2-pyridyl |
| 8G | 3-pyridyl |
| 8H | MeOOC–C₆H₄– (p-carbomethoxyphenyl) |
| 8I | 3,5-dimethylphenyl (Me at meta) |

2. The compound of of the structural formula

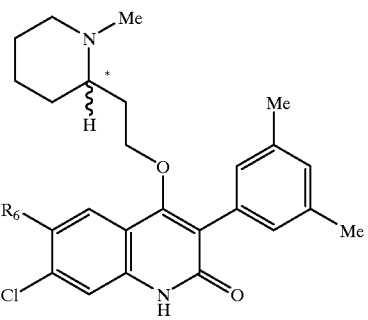

wherein $R_6$ is as indicated in the table below:

| Ex. # | $R_6$ |
|---|---|
| 9A | pyrimidin-4-yl-C(O)NH– (*S-enantiomer) |
| 9B | pyrimidin-4-yl-NHC(O)Me |
| 9C | pyrimidin-4-yl-NHC(O)Me (* S-enantiomer) |
| 9D | 2-methylpyrimidin-4-yl-NHC(O)Me (*S-enantiomer) |
| 9E | 2-cyclopropylpyrimidin-4-yl-NHC(O)Me (*S-enantiomer) |
| 9F | 2-(1-adamantyl)pyrimidin-4-yl-NHC(O)Me (*S-enantiomer) |

3. The compound of the structural formula
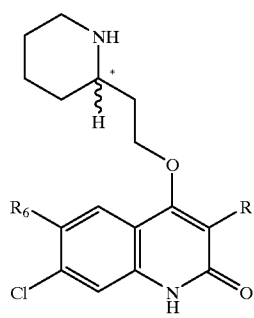
wherein R and R₆ are as indicated in the table below:

4. The compound of the structural formula
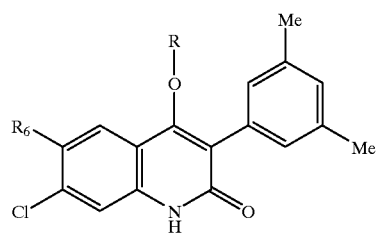

wherein R and $R_6$ are as indicated in the table below:

-continued

| Ex. # | R | R$_6$ |
|---|---|---|
| 11P | 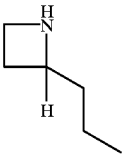 | 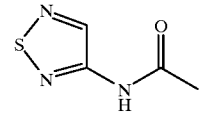 |
| 11Q | 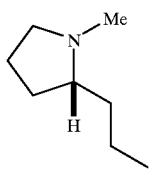 | 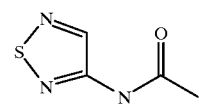 |
| 11R | 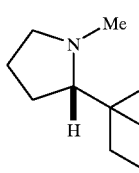 | 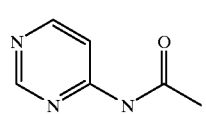 |
| 11S | 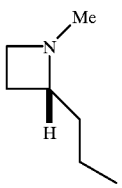 | 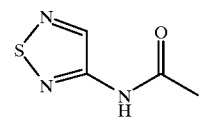 |

5. The compound of the structural formula

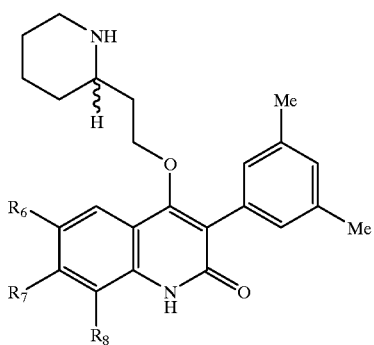

wherein R$_6$, R$_7$ and R$_8$ is as indicated in the table below:

| Ex. # | R$_6$ | R$_7$ | R$_8$ |
|---|---|---|---|
| 12A | H | 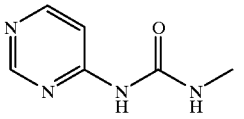 | H |

-continued

| Ex. # | R$_6$ | R$_7$ | R$_8$ |
|---|---|---|---|
| 12B | H | (pyrazinyl urea) | H |
| 12C | H | (pyrazinyl carboxamide) | H |
| 12D | H | (pyrazinyl urea) | Cl |
| 12E | H | (pyrimidinyl urea) | Cl |
| 12F | H | (chloropyrazinyl urea) | H |
| 12F | H | (chloropyrazinyl urea) | Cl |
| 12G | (pyrimidinyl acetamide) | CF$_3$ | H |
| | *S-enantiomer | | |
| 12H | (pyrimidinyl acetamide) | CF$_3$ | H |
| | *S-enantiomer, N-Me | | |

6. The compound of the structural formula

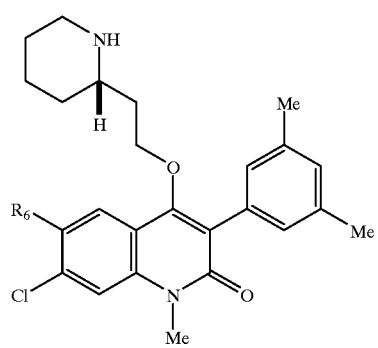

wherein $R_6$ is as indicated in the table below:

| Ex. # | $R_6$ |
|---|---|
| 13A | 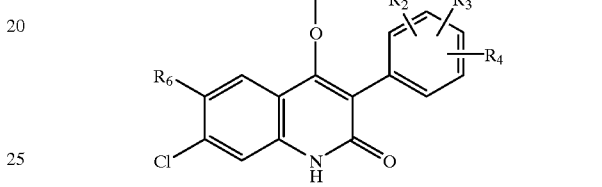 |
| 13B | (structure: pyrimidin-4-yl-NH-C(O)-N(Me)-Me) |

7. The compound of the structural formula (quinolinone structure with R, $R_2$, $R_3$, $R_4$, $R_6$)

wherein R, $R_2$, $R_3$, $R_4$ and $R_6$ are as indicated in the table below:

| Ex. # | R | $R_6$ | (1,2,5-thiadiazol-3-yl-NH-C(O)-) |
|---|---|---|---|
| 14A | (2-propylpiperidine, NH) | (pyrimidin-4-yl-NH-C(O)-Me) | (methylindane) |
| 14B | (2-propylazetidine, NH) | (pyrimidin-4-yl-NH-C(O)-Me) | (trimethylphenyl) |
| 14C | (2-propylazetidine, NH) | (1,2,5-thiadiazol-3-yl-NH-C(O)-Me) | (trimethylphenyl) |

-continued
| Ex. # | R | R6 | |
|---|---|---|---|
| 14D | 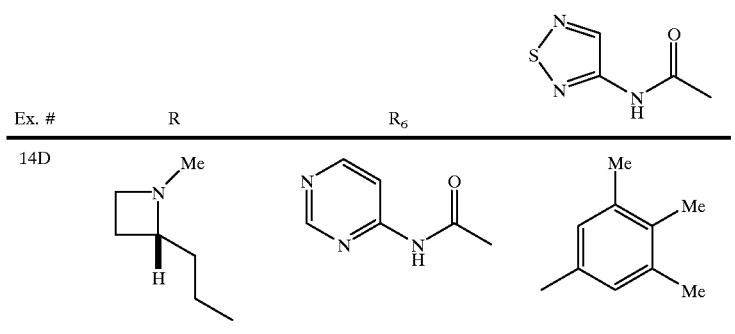 | | |
8. A compound of the formula
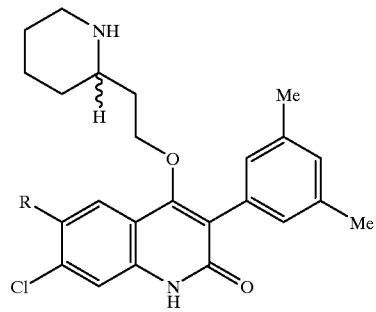
or a pharmaceutically acceptable addition salt and/or hydrate thereof, or where applicable, a geometric or optical isomer or racemic mixture thereof, wherein R is as indicated in the table below:
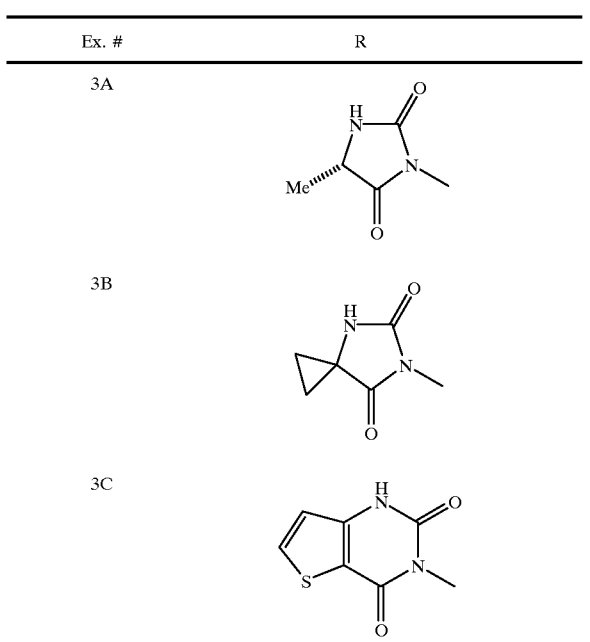
-continued
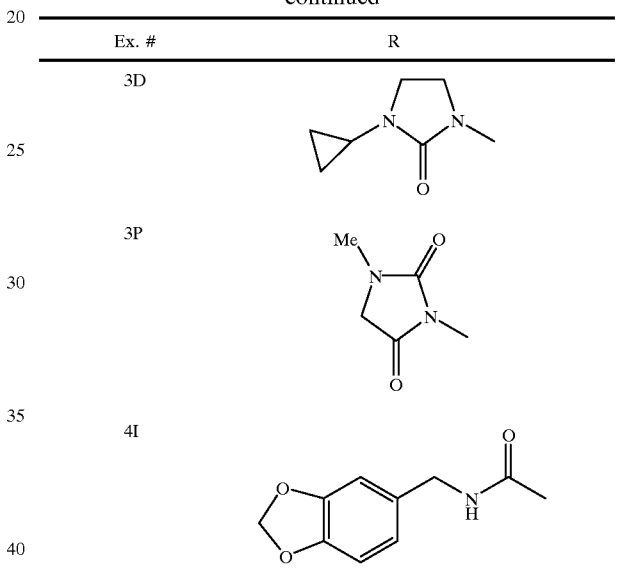
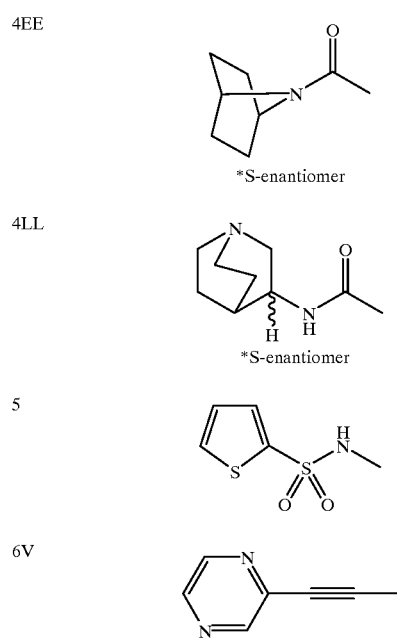

-continued

| Ex. # | R |
|---|---|
| 6W | (2-pyridyl)-C≡C-CH₃ |
| 12I | N-methyl-N'-(pyrazin-2-yl)-S-methyl-isothiourea |
| 12J | N-methyl-N'-(pyrazin-2-yl)-thiourea |
| 12K | N-cyclopropylamino-N'-methyl-N''-(pyrazin-2-yl)-guanidine |

9. A compound of the formula

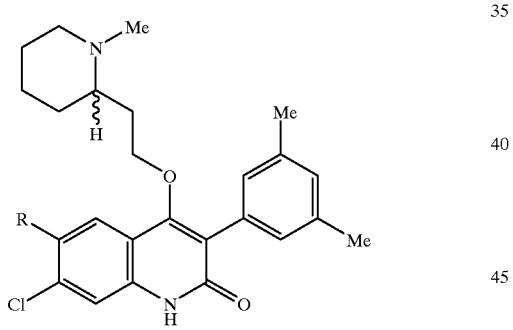

or a pharmaceutically acceptable addition salt and/or hydrate thereof, or where applicable, a geometric or optical isomer or racemic mixture thereof, wherein R is as indicated in the table below:

| Ex. # | R |
|---|---|
| 9G | 7-acetyl-7-azabicyclo[2.2.1]heptyl *S-enantiomer |

10. The compound the structural formula

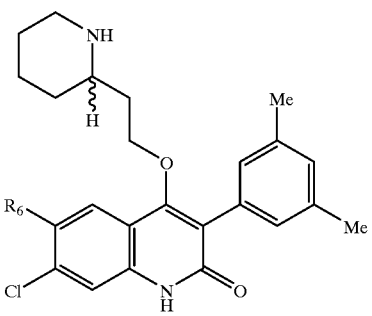

wherein $R_6$ is as indicated in the table below:

| Ex. # | $R_6$ |
|---|---|
| 1A | N-methyl-N'-(pyridin-2-yl)urea |
| 1B | N-methyl-N'-(pyridin-3-yl)urea |
| 1C | N-methyl-N'-(thiazol-2-yl)urea |
| 1D | N-methyl-N'-(1H-pyrazol-3-yl)urea |
| 1E | N-methyl-N'-(5-methyl-1,3,4-thiadiazol-2-yl)urea |
| 1F | N-methyl-N'-(pyrimidin-2-yl)urea |
| 1G | N-methyl-N'-(pyridin-4-ylmethyl)urea |
| 1H | N-methyl-N'-(pyridin-2-ylmethyl)methanediamine |

-continued
| Ex. # | R₆ |
|---|---|
| 1I | 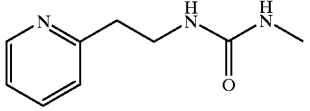 |
| 1J | 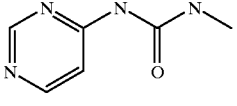 |
| 1K | 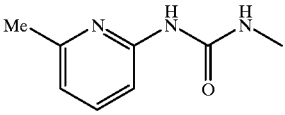 |
| 1L | 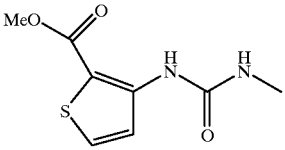 |
| 1M | 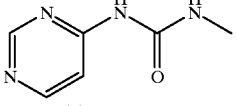<br>(S) enantiomer |
| 1N | 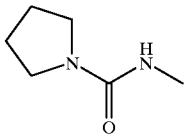 |
| 1O | 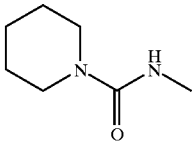 |
| 1P | 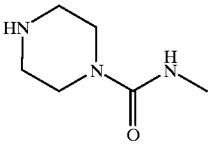 |
| 1Q | 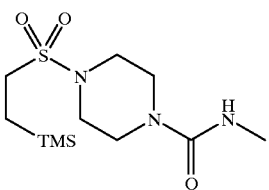 |
-continued
| Ex. # | R₆ |
|---|---|
| 1R | 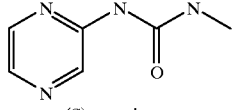<br>(S) enantiomer |
| 1S | 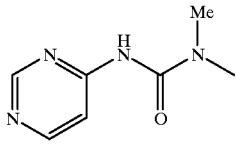 |
| 1T | 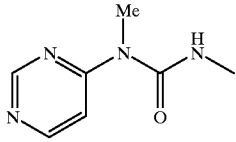<br>(S) enantiomer |
| 1U | 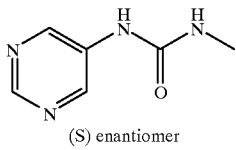<br>(S) enantiomer |
| 1V | 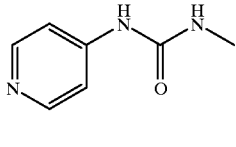 |
| 2A | 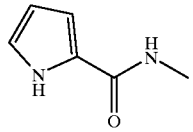 |
| 2B | 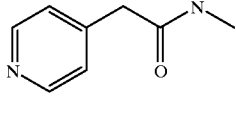 |
| 2C | 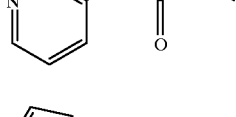 |
| 2D | 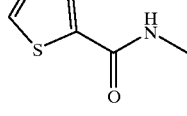 |
| 2E | 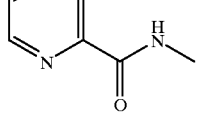 |

-continued
| Ex. # | R<sub>6</sub> |
|---|---|
| 2F |  S-enantiomer |
| 2G | 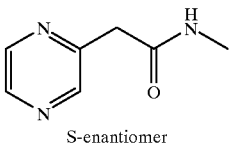 S-enantiomer |
| 2H | 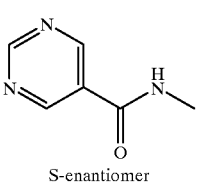 S-enantiomer |
| 2I | 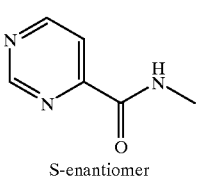 S-enantiomer |
| 2J | 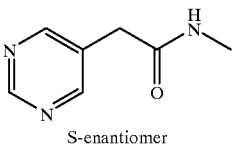 S-enantiomer |
| 2K | 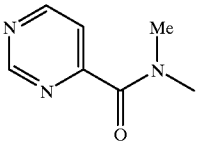 |
| 2L | 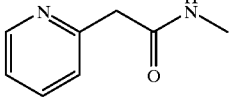 |
| 3E | 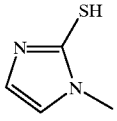 |
| 3F | 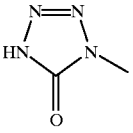 |
-continued
| Ex. # | R<sub>6</sub> |
|---|---|
| 3G | 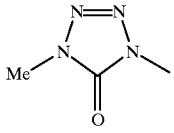 |
| 3H | 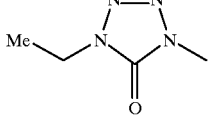 |
| 3I | 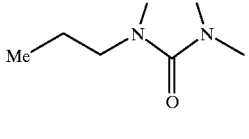 |
| 3J | 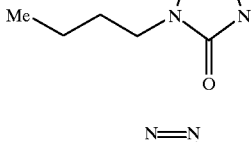 |
| 3K | 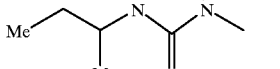 |
| 3L | 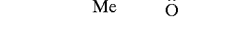 |
| 3M | 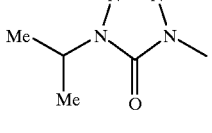 |
| 3N | 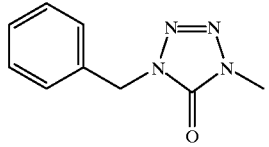 |
| 3O | 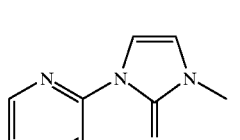 |
| 4A | 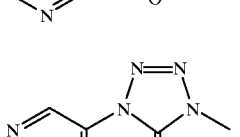 |

-continued
| Ex. # | R6 |
|---|---|
| 4B | 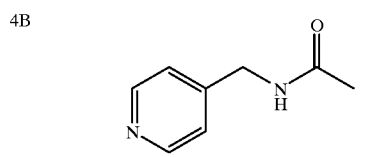 |
| 4C | 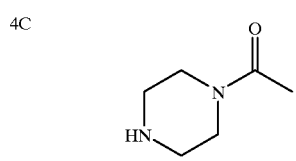 |
| 4D | 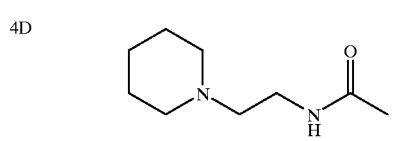 |
| 4E | 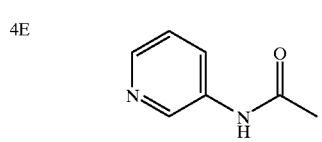 |
| 4F | 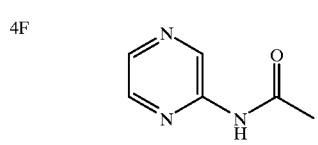 |
| 4G | 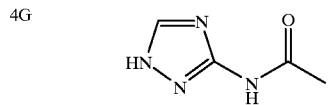 |
| 4H | 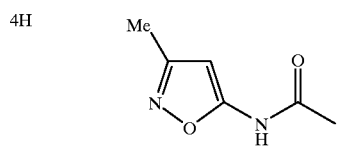 |
| 4J | 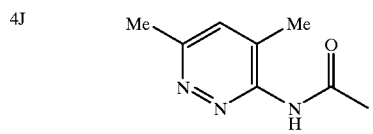 |
| 4K | 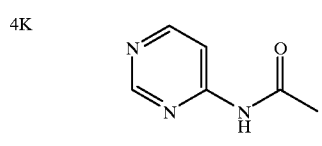 |
| 4L | 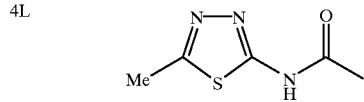 |
-continued
| Ex. # | R6 |
|---|---|
| 4M | 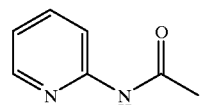 |
| 4N | 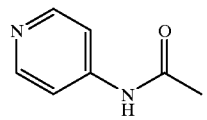 |
| 4O | 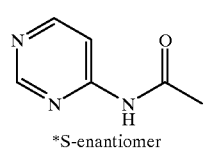<br>*S-enantiomer |
| 4P | 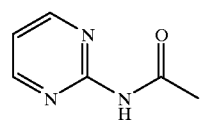 |
| 4Q | 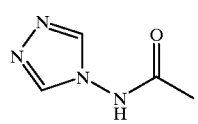 |
| 4R | 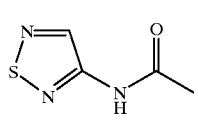 |
| 4S | 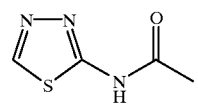 |
| 4T | 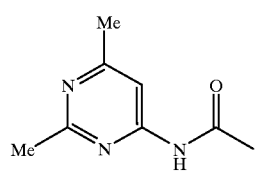 |
| 4U | 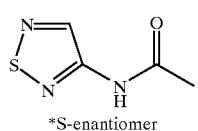<br>*S-enantiomer |
| 4V | 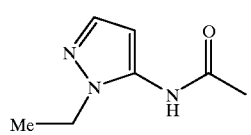 |

-continued
| Ex. # | R6 |
|---|---|
| 4W | 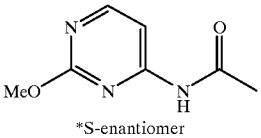 *S-enantiomer |
| 4X | *S-enantiomer |
| 4Y | *S-enantiomer |
| 4Z | *S-enantiomer |
| 4AA | *S-enantiomer |
| 4BB | |
| 4CC | *S-enantiomer |
| 4DD | *S-enantiomer |
| 4FF | *S-enantiomer |
-continued
| Ex. # | R6 |
|---|---|
| 4GG | 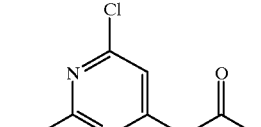 |
| 4HH | |
| 4II | *S-enantiomer |
| 4JJ | *S-enantiomer |
| 4KK | *S-enantiomer |
| 4MM | *S-enantiomer |
| 4NN | |
| 4OO | *S-enantiomer |
| 4PP | *S-enantiomer |

-continued
| Ex. # | R6 |
|---|---|
| 6A | 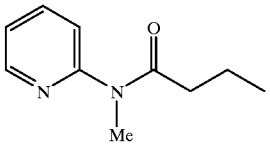 |
| 6B | 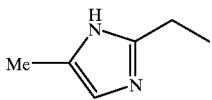 |
| 6C | 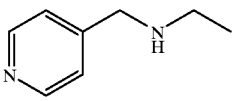 |
| 6D | 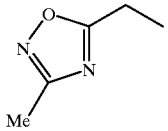 |
| 6E | 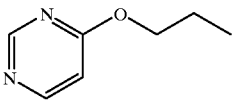 |
| 6F | 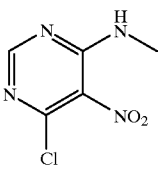 |
| 6G | 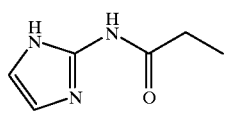 |
| 6H | 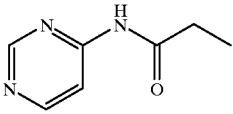 |
| 6I | 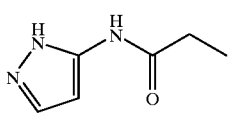 |
| 6J | 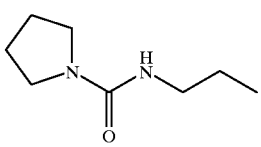 |
-continued
| Ex. # | R6 |
|---|---|
| 6K | 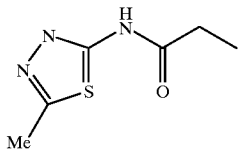 |
| 6L | 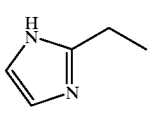 |
| 6M | 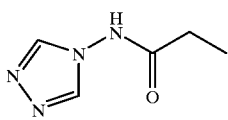 |
| 6N | 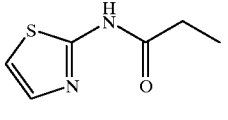 |
| 6O | 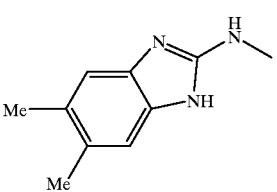 |
| 6P | 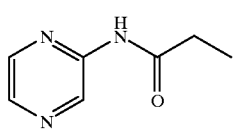 |
| 6Q | 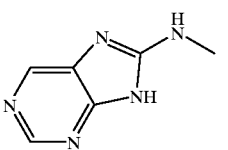 |
| 6R | 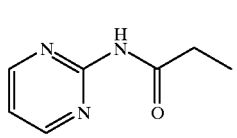 |
| 6S | 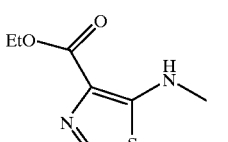 |
| 6T | 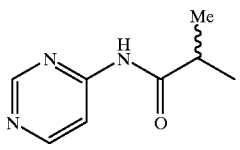 |

-continued
| Ex. # | R$_6$ |
|---|---|
| 6U | 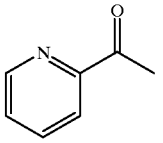 |
| 6X | 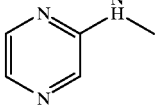 |
| 6Y | 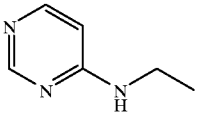 |
| 6Z | 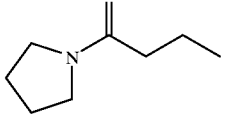 |
| 7A | 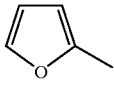 |
| 7B | 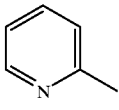 |
-continued
| Ex. # | R$_6$ |
|---|---|
| 7C | 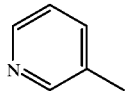 |
| 7D | 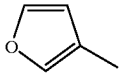 |
| 7E | 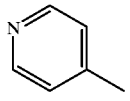 |
| 7F | 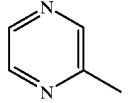 |
| 7G | 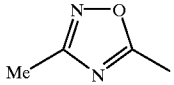 |
| 7H | 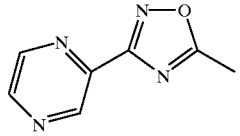 |
* * * * *